(12) United States Patent
Giancaspro et al.

(10) Patent No.: US 8,234,093 B2
(45) Date of Patent: Jul. 31, 2012

(54) COMPUTATIONAL METHOD FOR LOAD ENHANCEMENT FACTORS

(75) Inventors: James W. Giancaspro, Miami Beach, FL (US); Winson Taam, Sammamish, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 12/965,876

(22) Filed: Dec. 12, 2010

(65) Prior Publication Data

US 2011/0144924 A1 Jun. 16, 2011

Related U.S. Application Data

(62) Division of application No. 11/643,960, filed on Dec. 22, 2006, now Pat. No. 7,877,229.

(51) Int. Cl.
*G06F 17/10* (2006.01)
*G06F 17/18* (2006.01)
(52) U.S. Cl. ............ 702/179; 702/34; 702/35; 702/42; 703/2; 703/7
(58) Field of Classification Search .............. 702/179, 702/34, 35, 42
See application file for complete search history.

(56) References Cited

U.S. PATENT DOCUMENTS

| | | | |
|---|---|---|---|
| 4,590,804 A * | 5/1986 | Brull | 73/762 |
| 6,671,647 B2 | 12/2003 | Ishii et al. | |
| 6,763,312 B1 | 7/2004 | Judd | |
| 6,996,493 B1 | 2/2006 | Sikora et al. | |
| 2002/0013643 A1* | 1/2002 | Ishii et al. | 700/289 |
| 2004/0138832 A1* | 7/2004 | Judd | 702/56 |
| 2007/0239368 A1 | 10/2007 | Marrano et al. | |
| 2009/0240646 A1* | 9/2009 | Tryon, III | 706/52 |

OTHER PUBLICATIONS

R.S. Whitehead, H.P. Kan, R. Cordero, E.S. Saether: "Certification Testing Methodology for Composite Structure, vol. I-Data Analysis"; Oct. 1986.
Todd S. Gross, Steven Lampman, "Micromechanisms of Monotonic and Cyclic Crack Growth," pp. 42-60, 1996.
R.S. Whitehead, H.P. Kan, R. Cordero, E.S. Saether: "Certification Testing Methodology for Composite Structure, vol. II-Methodology Development"; Oct. 1986.
Department of Defense—United States of America: "Composite Materials Handbook vol. 3, Polymer Matrix Composite Materials Usage, Design, and Analysis"; Jun. 17, 2002.
R. Wong, R. Abbott, "Durability & Damage Tolerance of Graphite/Epoxy Honeycomb Structures," Proceedings of the 35th International SAMPE Symposium, Anaheim, CA, Apr. 2-5, 1990, pp. 366-380.
International Search Report, PCT US2007/088614, mailed Jun. 16, 2008.

(Continued)

*Primary Examiner* — Hal Wachsman

(57) ABSTRACT

The computation of a Load Factor, a Life Factor or a Load Enhancement Factor using Modified Joint Weibull Analysis may include retrieving a test data set from at least one database and analyzing the data retrieved for fit with a Weibull distribution model. The test data may be analyzed to determine if at least two coupons have been tested and if applied loads and duration of testing at a component-level were varied. A shape parameter may be calculated for the Weibull distribution model. A scale parameter may be calculated for the Weibull distribution of the data. A stress to life cycle relationship may be calculated to account for scatter in the data through the Weibull distribution data. The Life Factor, the Load Factor or the Load Enhancement Factor may be calculated based on the stress to life cycle relationship to account for scatter.

37 Claims, 7 Drawing Sheets

OTHER PUBLICATIONS

Fritz Scholz, "Unified Confidence Bounds for Censored Weibull Data With Covariates," Mathematics & Computing Technology, Apr. 1, 2002, pp. 1-32, The Boeing Company, Seattle, WA.

Ric Abbott & Ann L. Kolarik, Strength Substantiation of All the Composite Airframe (A Materials Data Base Approach): 34th International SAMPE Symposium, May 8-11, 1989, pp. 283-289, Beech Aircraft Corporation, Wichita Kansas.

J.A Collins, "High-Cycle Fatigue" (Chapter 7) from Failure of Materials in Mechanical Design: 1993, pp. 178-254.

W. Nelson, "Applied Life Data Analysis," 1982, pp. 36-45.

W.O. Meeker & L.A. Escobar, "Failure-Time Regression Analysis" (Chapter 17) from "Statistical Methods for Reliability Data," 1998, pp. 427-447.

G.P. Sendeckyj "Fitting Models to Composite Materials Fatigue Data," from "Test Methods and Design Allowables for Fibrous Composites," 1981, pp. 245-260, ASTM STP 734, C.C. Chamis, Ed., American Society for Testing and Materials.

Ric Abbott, "Design and Certification of the All-Composite Airframe," SAE Technical Paper Series, Document #892210, Aerospace Technology Conference and Exposition, Sep. 25-28, 1989, Anaheim, CA, whole document.

J.M. Ruiz Barragan, M.A. Morell Fuentes, M.H. Garcia and D.F. Villalba, "Load Enhancement Factor to Be Applied on Fatigue Test for Certification of Composites," Proceedings of the Twenty-First International Committee on Aeronautical Fatigue Symposium, Jun. 27-29, 2001, Toulouse, France, pp. 313-329.

Wohler, "Wohler's Experiments on the Strength of Metals," Aug. 23, 1867, excerpt of article.

J. Lameris, "The Use of Load Enhancement Factors in the Certification of Composite Aircraft Structures," Feb. 22, 1990, pp. 1-58, National Aerospace Laboratory, NLR, Amsterdam, The Netherlands.

J. Lawless, "Statistical Models and Methods for Lifetime Data," 1982, pp. 298-313, Wiley & Son, New York, whole document.

B. Brandecker & R. Hilgert, "A320 Full Scale Structural Testing for Fatigue and Damage Tolerance Certification of Metallic and Composite Structure," 1988, pp. 1244-1256.

R. Abbott, "Load Enhancement Factor for Composite Test Spectra (Raytheon Method)," Damage Tolerance Workshop, Jul. 2006, whole document.

H.R. Ashton, "Damage Tolerance and Durability Testing for F/A-18 EIF Composite Materials Structures," 1996, pp. 1-13, American Institute of Aeronautics and Astronautics, Inc.

B. Harris, N. Gathercole, Ja Lee, H. Reiter, T. Adam, "Life prediction for constant-stress fatigue in carbon-fibre composites," Phil. Trans. R. Soc. Lond. A, 1997, pp. 1259-1294, vol. 355, Great Britain.

Wayne Nelson, "Fitting of Fatigue Curves with Nonconstant Standard Deviation to Data with Runouts," Journal otTesting and Evaluation, JTEVA, Mar. 1984, pp. 69-77, vol. 12, No. 2.

K.B. Sanger, "Certification Testing Methodology for CompOSite Structures," Report No. NADC-86132-60, Jan. 1986, pp. 1-159.

Fritz Scholz, "Weibull and Gumbel Distribution Exact Confidence Bounds," Research and Technology-Boeing Computer Services, May 13, 1994, pp. 1-49.

O. Gogkol, "A310-300 CFRP FIN Damage Tolerance Demonstration," article from High Tech—the Way into the Nineties, 1986. pp. 273-286, Elsevier Science Publishers B.V., Amsterdam, The Netherlands.

* cited by examiner

COMPUTATIONAL METHOD FOR LOAD ENHANCEMENT FACTORS

CROSS-REFERENCE TO RELATED APPLICATIONS

The present application is a divisional of and claims priority to application Ser. No. 11/643,960, now U.S. Pat. No. 7,877,229, entitled COMPUTATIONAL METHOD FOR LOAD ENHANCEMENT FACTORS AND APPARATUS FOR EXECUTING SAME filed on Dec. 22, 2006, the entire contents of which is incorporated by reference herein.

FIELD

The present disclosure relates generally to a computational method for determining performance of composite structures. More particularly, the present disclosure relates to a computational methodology for determining a Load Enhancement Factor (LEF) for more accurate and cost effective testing of composite structures and associated software and hardware to execute the methodology.

BACKGROUND

Composite structures are advantageous over metallic structures in a number of ways, including corrosion resistance, reduced weight, and fatigue performance. However, the modes in which damage initiation and progression or fatigue occur are complex and extremely difficult to model analytically in comparison to traditional metallic structures.

As a result, certifying the durability of composite structures relies heavily upon experimental fatigue tests. Since fatigue scatter in composites has been, in general, much higher than in metallic components, experimental fatigue tests must be conducted on many replicates to achieve the desired levels of reliability in comparison with the same tests when performed on metallic structures. Carrying out such a vast array of experimental tests dramatically increases the cost and time necessary to complete certification of parts, particularly in the aerospace industry. In an attempt to account for the effects of fatigue scatter and to reduce the time and cost associated with testing components containing composite structures, a number of statistically based fatigue testing approaches have been developed. One such methodology uses the Load Enhancement Factor (LEF) approach originally developed by the Naval Air Development Center (NADC) in conjunction with Northrop Corporation in the 1980's in a series of papers on computational methods for computing fatigue life and residual strength in composites and certification methodologies. The tests generally include coupon testing and component testing. A "coupon" is a simple specimen constructed to evaluate a specific property of a material and a "component" is generally a more complex structure made from this material.

The new LEF approach was developed to overcome the individual disadvantages of the Load Factor and Life Factor approaches presented in, for instance, Ratwani, M. M. and Kan H. P., "Development of Analytical Techniques for Predicting Compression Fatigue Life and Residual Strength of Composites," NADC-82104-60, March 1982 and Sanger, K. B., "Certification Testing Methodology for Composite Structures," Report No. NADC-86132-60, January 1986. The Load Factor and Life Factor approaches are limited as they require either a high experimental test load which may exceed the static strength of the test material or component or require exceedingly long test periods. The LEF method uses these factors in concert to achieve both reasonable test durations and test loads that are well below the static strength of the component. However, the traditional methodology for determining LEF has been misused, resulting in the consistent use of an LEF value of 1.15 to represent all composite materials.

This approach has continued to be used, unmodified, over the past two decades. However, composite materials and the technology to apply and build from them have advanced considerably in the past two decades. In retrospect, the approach of the traditional method of calculating LEF relies on many questionable assumptions, is difficult to comprehend, and has a number of significant limitations. This has resulted in a number of inconsistencies and inaccuracies in the manner in which Load Enhancement Factors have been applied to fatigue testing on the component level in the past.

The traditional LEF methodology possesses a number of limitations and drawbacks, which render it difficult to employ and reduce its accuracy and applicability. The LEF methodology was derived using a "typical" stress-life (S-N) curve as a foundation. The papers outlining the development of the traditional LEF methodology identify $P_M$ as static strength. However, the equations used to derive the traditional methodology do not make use of static strength, $P_M$ in the equations. Therefore, this approach does not account for scatter in static strength, an assumption that is never identified by the methodology, but is implicit in the development of the equations. As composites have a high degree of scatter in static strength, this is a significant shortcoming of the traditional LEF approach.

Whitehead, et al., entitled "Certification Testing Methodology for Composite Structures," Vols. I and II, October 1986, ("Whitehead"), a paper setting forth the traditional LEF approach, proposed to compute the LEF through Joint Weibull Analysis, which can be utilized to compute the shape and scale parameters assuming a Weibull distribution by measuring scatter within groups, for instance groups of fatigue stress levels, as set forth in volume I of the paper entitled "Certification Testing Methodology for Composite Structures". Coupons must be grouped into distinct stress levels with many replicates per level. The authors provided the following equation listed below and recited as Equation 10 on Page 12 of Whitehead Vol. I to compute the shape ($\hat{a}$) and scale ($\hat{\beta}$) parameters, (Whitehead Vol. I, Eq. 10)

$$\sum_{i=1}^{M}\left(\frac{\sum_{j=1}^{n_i} x_{ij}^{\hat{a}} \ln x_{ij}}{\sum_{j=1}^{n_i} x_{ij}^{\hat{a}}}\right) - \frac{M}{\hat{a}} - \left[\sum_{i=1}^{M} \frac{\sum_{j=1}^{n_{fi}} \ln x_{ij}}{n_{fi}}\right] = 0$$

where:
$n_i$ (i=1, 2 ..., M) is the number of data points in the $i^{th}$ group of data
$n_{fi}$ (i=1, 2 ..., M) is the number of failures in the $i^{th}$ group of data.
This equation is defined in terms of $\hat{a}$ so an iterative procedure must be used to arrive at a solution.

Once $\hat{a}$ is computed, the other Weibull parameters (scale parameters) can be determined using the following equation listed below and recited as Equation 11 on Page 12 of Whitehead Vol. I, (Whitehead Vol. I, Eq. 11)

$$\hat{\beta}_i = \left[\frac{1}{n_{fi}} \sum_{j=1}^{n_i} x_{ij}^{\hat{\alpha}}\right]^{\frac{1}{\hat{\alpha}}}$$

On the surface, both equations appear to be valid. However, if equation (Whitehead Vol. I, Eq. 10) is dissected and rearranged slightly, the result is the following, $$\frac{\hat{\alpha}\left[\sum_{i=1}^{M}\left(\frac{\sum_{j=1}^{n_i} x_{ij}^{\hat{\alpha}} \ln x_{ij}}{\sum_{j=1}^{n_i} x_{ij}^{\hat{\alpha}}}\right) - \left[\sum_{i=1}^{M} \frac{\sum_{j=1}^{n_{fi}} \ln x_{ij}}{n_{fi}}\right]\right]}{M} = 1$$

In this form, the denominator on the left side of the equation is M, the total number of groups—here groups of fatigue stress levels. Therefore, the left side of the equation is merely an average value of M groups. The traditional methodology using Joint Weibull analysis does not identify the implications of using this simple statistical average in estimating the parameters. However, this method is severely limited. By using an average, the equation is only valid for stress levels with the same number of tested and failed coupons. In addition, this equation implies that $n_{fi}$, the number of failures for a given stress level, must be equal for all stress levels. This significantly reduces the applicability of the method.

An S-N curve is typically developed using a number of specimens that are tested over varying stress levels to examine the effect of stress level on fatigue life. The general pattern of stress-life relationship shows that as stress increases life decreases, or in other words, higher levels of stress reduce life expectancy in a component.

However, using the traditional LEF approach and a traditional S-N curve, as previously stated, typically few if any of the data points in this type of relationship may be utilized to determine an LEF with an accounting of scatter as there is non-identical stress levels being tested and, typically, an uneven number of tested and failed coupons exists. To account for scatter in fatigue life, the traditional method using Joint Weibull Analysis requires identical specimens be tested at multiple identical stress levels for the comparison.

Furthermore, although the traditional LEF method clearly states that environmental conditions, specimen geometry, and numerous other variables affect the Weibull shape parameters, the method still uses these modal values "for simplicity," as stated on page 82 of Whitehead, Vol. I. In addition, the reference claims that these modal values are "lower than mean values and, therefore, represent conservative values." While the traditional LEF method with Joint Weibull Analysis may be correct in stating that the modal values may be less than the mean values for this particular literature review, these values do not necessarily represent conservative values for all composite materials, environmental conditions, specimen configurations, and other unknown variables. This is a potentially unsafe assumption.

Using these shape parameters values, the traditional LEF without Joint Weibull Analysis method then substitutes them into the following equation listed below and recited as Equation 17 on Page 46 of Whitehead Vol. II:

(Whitehead Vol. II, Eq. 17)

$$F = \frac{\mu \Gamma\left(\frac{\alpha_R + 1}{\alpha_R}\right)}{\left[\frac{-\ln(p)}{\chi_\gamma^2(2n)/2n}\right]^{\frac{1}{\alpha_R}}}$$

This assumes particular modal shape parameters for fatigue life and for residual strength, a single component-level test for a duration of 1.5 lifetimes at the B-Basis level (95% confidence with 90% reliability), the resulting LEF value was computed at approximately 1.15. Despite the widespread use of this LEF value (1.15), little data exists which substantiates the LEF values that engineers have employed on component tests. However, it is frequently assumed from the publication of this initial NADC value that these values can be repeatedly used and have been used on a wide number of composite compositions and structures being tested. In numerous published cases, the computations used to arrive at the LEF, Life Factors, etc. are absent from the documentation. Since many of these cases invoke the use of an LEF of 1.15, it is reasonable to assume that the engineers simply used the shape parameters and LEF values provided in the NADC document without quantifying the scatter of their specific materials under investigation.

However, due to the widespread variability in manufacturing processes, advances in composites, variations and advances in laminate design, and marked increases in the complexity of theses designs, material types, loading configurations, and the like, the LEF value of 1.15 when used, though assumed initially to be conservative, may in fact be unconservative given the large quantity of unknown variables.

Yet another confusion in the NADC approach is that static strength was used in the analysis. Residual strength will usually exhibit much more variability since damage has been induced in the material being tested, unlike static strength, which represents a material in a pristine condition. Using the static strength to compute a "representative" shape parameter is contradictory since static strength is never used in the derivation of the traditional LEF equations.

To overcome some of these drawbacks when testing on the coupon-level, if data already exists in this form, namely, one replicate per stress level, an alternative approach called "Weibull Regression for LEF Determination" can be utilized. This alternative approach can be used to model the S-N relationship, and then to develop LEF under that model.

The shortcomings, assumptions, and omissions of the traditional LEF computation methodology are further perpetuated and compounded by the use of these values in dramatically different geometric configurations, environments, manufacturing methods, and similar variables for composite structures. For example, some materials, such as aramid (sold under the trade name KEVLAR), are prone to substantial fatigue scatter when exposed to environments saturated with moisture.

Furthermore, certain loading conditions are prone to more scatter than others are. For example, laminate composites manufacturing using thick braids or tapes with large tow sizes exhibit more scatter in compressive loading (due to local buckling effects) than in tension loading. None of these factors is accommodated by the traditional method of calculating LEF. This result is another limitation in LEF analyses derived by the traditional LEF methodology. The failure to develop LEF analyses that consider a number of environmental variables, scatter in static strength, and other variables commonly at play in composite structure loading is a significant drawback to current testing practices.

Based upon these weaknesses, the approach that the traditional LEF methods take in generalizing the Weibull shape parameters and the resulting LEF value of 1.15 is of questionable merit and difficult to accept given the increasing number of unaccounted variables. Accordingly, the shape parameters and corresponding values should not be generalized or applied to all composite materials and a more comprehensive testing methodology is needed.

A new methodology for approaching the computation of the LEF incorporating the characteristics of scatter, residual strength, geometry and environmental variables and scatter in residual strength and fatigue life is needed to reduce costs, increase safety, and increase reliability. Due to the inherent cost and extended duration of testing of composite and metallic structures on the component-level, it is often desired to accelerate testing while still maintaining the desired level of statistical reliability and confidence. By adjusting both the load levels and planned duration of a component-level fatigue test without altering the statistical reliability, both the time and cost of the test may be reduced. Additionally, greater accuracy and higher levels of safety need to be achieved by a more accurate method of calculating the LEF accounting for residual strength and variations in residual strength through scatter. Accordingly, it is desirable to provide a method and an apparatus executing the method of improved computation of Load Enhancement Factors that is capable of overcoming the disadvantages described herein at least to some extent.

SUMMARY

The foregoing needs are met, to a great extent, by the embodiments disclosed herein. In one aspect, an apparatus improves the computation of Load Enhancement Factors. According to another aspect, a method computes a value for LEF incorporating the characteristics of scatter, residual strength, geometry, environmental variables and other heretofore unaccounted variables. Such a method may reduce costs, increase safety, and increase reliability. By adjusting both the load levels and planned duration of a component-level fatigue test without altering the statistical reliability, both the time and cost of testing may be reduced. Additionally, greater accuracy and higher levels of safety may be achieved by this more accurate method of calculating the LEF that accounts for residual strength and variations in residual strength through scatter. Accordingly, a method of improved computation of Load Enhancement Factors and an apparatus for executing the same are provided.

An embodiment relates to a method of calculating a load enhancement factor. In this method, a data set may be retrieved from at least one database and the data may then be analyzed for fit with a statistical distribution model. Then proceeding to analyze the data retrieved for statistical conditions. Based on the conditions, calculating a stress to life cycle relationship accounting for scatter in the test data and calculating a Load Enhancement Factor based on the stress to life cycle relationship.

Another embodiment pertains to a method of performing a Modified Joint Weibull Analysis, where the method may retrieve test data. The method may then analyze the data retrieved for fit with a Weibull distribution model for the data and analyzes the test data set retrieved to determine if at least two coupons have been tested and if both the applied loads and duration of testing at the component-level were varied. The method may then compute an one shape parameter for the Weibull distribution model for fatigue life data, and one for residual strength data. The method may compute at least one scale parameter for the Weibull distribution of the data and stores the at least one scale parameter. The method may proceed to compute a Life Factor, a Load Factor and a Load Enhancement Factor based on the shape parameters thereby accounting for scatter in the test data. The Load Enhancement Factor may be determined by setting a confidence level, a reliability level, test duration and the number of component to be tested.

Yet another embodiment relates to a method of performing a Weibull regression analysis. The method may obtain coupon test data and may apply a Weibull distribution regression function to the coupon test data to estimate stress to fatigue life curve and applies an equation to relate the log of a scale parameter of the Weibull distribution regression function with the log of a stress level of the stress to fatigue life curve. The method may implement an estimation procedure to incorporate the stress to fatigue life relationship in the computation of the Load Enhancement Factor through the intercept and slope of the estimates of the stress to fatigue life curve ($\hat{\theta}_0$, $\hat{\theta}_1$). The method may further determine a confidence level and using a variance and a co-variance matrix developed from the estimation procedure to compute the Load Enhancement Factor.

The apparatus according to a number of embodiments may include a computer programmed with software to operate the general purpose computer in accordance with an embodiment. In some embodiments, the apparatus may include a database with coupon test data and a computer configured to apply a Weibull distribution regression function to the coupon test data to develop an estimated stress to fatigue life curve and apply an equation to relate the log of a scale parameter of the Weibull distribution regression function with the log of a stress level of the stress to fatigue life curve. The apparatus may implement an estimation procedure to incorporate the stress to fatigue life relationship in the computation of the Load Enhancement Factor through the intercept and slope of the estimates of the stress-to-fatigue life curve ($\hat{\theta}_0$, $\hat{\theta}_1$); thereby obtaining a confidence level and using a variance and a co-variance matrix developed from the estimation procedure to compute the Load Enhancement Factor.

There has thus been summarized some of the embodiments in order that the detailed description thereof herein may be better understood, and in order that the contribution of any one of the embodiments to the art may be better appreciated. There are, of course, additional embodiments that will be described below and which will form the subject matter of the claims appended hereto.

In this respect, before explaining at least one embodiment in detail, it is to be understood that the claims herein are not limited in their application to the details of construction and to the arrangements of the components set forth in the following description or illustrated in the drawings. Various embodiments may be practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes described herein. It is important, therefore, that the claims be regarded as including such equivalent constructions.

DETAILED DESCRIPTION OF THE EMBODIMENTS

Figure 1:
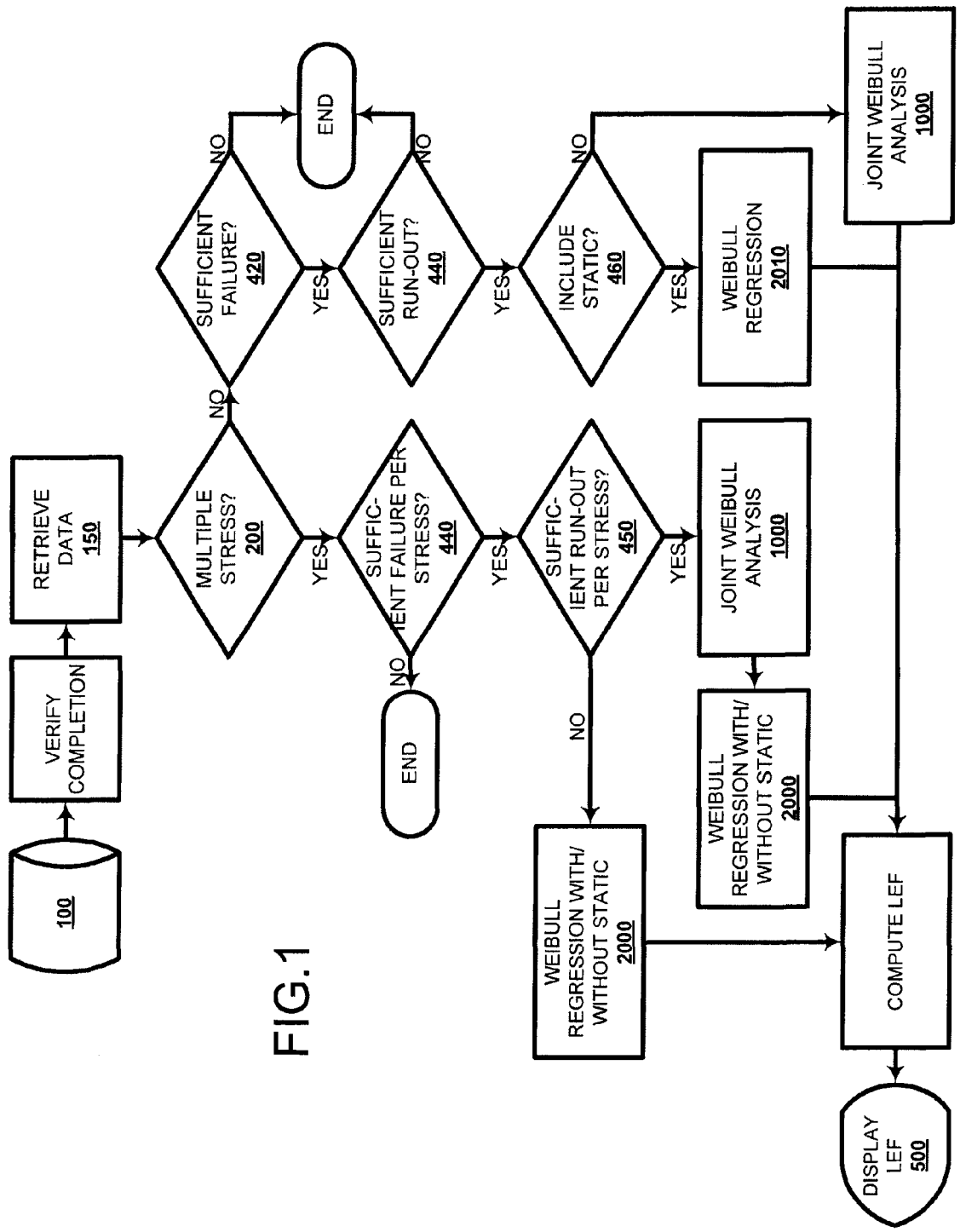
FIG. 1 is a flow diagram illustrating steps for processing data to compute LEF according to an embodiment.

The following definitions are applicable throughout:

The term "computer" or "computer system" refers to any apparatus that is capable of accepting a structured input, processing the structured input according to prescribed rules, and producing results of the processing as output. Non-limiting, non-exhaustive examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

A "computer-readable medium" refers to any storage device used for storing data accessible by a computer. Examples of a computer-readable medium include: a magnetic hard disk; a floppy disk; an optical disk, such as a CD-ROM and a DVD; a magnetic tape; a memory chip or jump drive; flash memory; and a carrier wave used to carry computer-readable electronic data, such as those used in transmitting and receiving packetized information, e-mail or in accessing a network.

The term "Software" refers to prescribed rules to operate a computer. Non limiting, non-exhaustive examples of software include: software; code segments; instructions; computer programs; and programmed logic.

A "computer system" refers to a system having a computer, where the computer comprises a computer-readable medium embodying software to operate the computer.

A "network" refers to a number of computers and associated devices that are connected by communication facilities. A network may include permanent connections such as cables and/or temporary connections such as those made through telephone or other communication links. Examples of a network include: an internet, such as the Internet; an intranet; a local area network (LAN); a wide area network (WAN); and a combination of networks, such as an internet and an intranet.

An "information storage device" refers to an article of manufacture used to store information. An information storage device has different forms, for example, paper form and electronic form. In paper form, the information storage device includes paper printed with the information. In electronic form, the information storage device includes a computer-readable medium storing the information as software, for example, as data.

The term "A-basis" refers to the 95% confidence limit for 99% reliability or a value above which at least 99% of the population of the values are expected to fall, with a confidence of 95%.

The term "B-basis" refers to a 95% confidence limit for 90% reliability or a value above which at least 90% of the population of values is expected to fall, with a confidence of 95%.

The following abbreviations are used herein:

B(S) represents a B-basis value in fatigue cycle at stress S.

B(X/S) represents the B-basis value in residual strength at X run-out cycles and stress S.

E(W/X,S) represents the expected residual strength at X run-out cycles and stress S.

E(X/S) represents the expected fatigue failure cycle at stress S.

$f(.)$ represents a probability density function.

$F(.)$ represents a cumulative probability function (also called a distribution function).

i represents a Group number corresponding to a particular stress level for coupon-level testing (used in Joint Weibull analysis) e.g. i=1, 2, 3, . . . .

j a Data point (element) within $i^{th}$ group.

LEE represents Load Enhancement Factor.

M represents Total number of groups (stress levels) for coupon-level testing.

$n_0$ represents Number of planned component-level tests (sample size used in future test planning)

$n_{f_i}$ represents Number of coupons failed during fatigue in the group (stress level).

$n_i$ represents the number of coupons in the group (stress level).

$n_L$ represents the total number of coupons used in the Weibull model for fatigue life cycle (total number of coupons tested in fatigue).

$n_r$ represents the total number of coupons used in the Weibull model for residual strength.

$n_{r_i}$ represents the number of coupons used in the Weibull model for residual strength in the $i^{th}$ group (stress level); number of coupons surviving the fatigue test to run-out.

$n_s$ represents the number of coupons tested for static strength.

N represents the design life (in number of lifetimes) at the desired reliability.

$N_0$ represents the test duration (in number of lifetimes) for component-level testing.

$N_i$ represents the design life at desired reliability for $i^{th}$ stress level.

$N_F$ represents the Life Factor derived from coupon-level fatigue testing.

$N_{M_i}=E(X/S)$ represents the mean life for each stress level for coupon-level testing; keep it but define it as equal to E(X/S).

$P_{T_i}$ represents the mean residual strength per stress level.

$R(.)$ represents the reliability function; desired level of reliability.

S represents the stress level applied in fatigue test or static strength.

$S_1$ represents the fatigue stress level applied to component to achieve desired reliability with test duration of 1 lifetime.

$S_2$ represents the fatigue stress level applied to component to achieve desired reliability with test duration of equal to the Life Factor.

$S_A$ represents the stress level computed from the A-basis value of the fatigue cycle distribution.

$S_B$ represents the stress level computed from the B-basis value of the fatigue cycle distribution.

$S_E$ represents the stress level computed from an expected value of the fatigue cycle distribution.

$S_F$ represents the load factor.

$S_j$ represents the static strength of j data point for coupon-level testing.

$S_M$ represents the mean static strength.

$S_r$ represents the static strength allowable.

W represents the residual strength at X run-out cycle and stress S.

$W_{r_i}$ represents the residual strength allowable for $i^{th}$ stress level.

X represents the number of fatigue cycles to failure or to "run-out" for a coupon.

$X_1$ represents the number of cycles on the coupon level that defines one lifetime.

$Y=\ln(X)$ represents the natural logarithm of fatigue cycle.

$\alpha$ represents the scale parameter of a two-parameter Weibull distribution.

$\alpha_{Li}$ represents the scale parameter of the Weibull model for fatigue life measured from coupon-level testing for $i^{th}$ group (stress level).

$\alpha_{r_i}$ represents the scale parameter of the Weibull model for residual strength measured from coupon-level testing for $i^{th}$ group (stress level).

$\alpha_s$ represents the scale parameter of the Weibull model for static strength measured from coupon-level testing.

$\beta$ represents the shape parameter of a two-parameter Weibull distribution, also known as the Weibull slope.

$\beta_L$ represents the shape parameter of the Weibull model for fatigue life measured from coupon-level testing.

$\beta_r$ represents the shape parameter of the Weibull model for residual strength measured from coupon-level testing.

$\beta_s$ represents the shape parameter of the Weibull model for static strength measured from coupon-level testing.

$\beta_{SN}$ represents the shape parameter for Weibull regression model.

$\delta$ represents the dimensionless parameter equal to 1 if X is a fatigue failure, equal to 0 if X is a "run-out".

$\gamma$ represents the confidence level.

$\Gamma$ represents the gamma function.

$K(N_0)$ represents the scaling coefficient in the Load Enhancement Factor to ensure that LEF=1 when the test duration is $N_F$.

$\theta_0$ represents the intercept parameter of the Weibull regression model.

$\theta_1$ represents the slope parameter of the Weibull regression model.

$\chi_{\gamma,\nu}^2$ represents the Chi-square random variable with $\gamma$ confidence level and $\nu$ degrees of freedom.

An embodiment includes a method of computing load enhancement factors and an apparatus for performing the same. The application of load enhancement factor involves raising the stress level in test and reducing test duration in such a way that a desired reliability is demonstrated when no failure is observed. Testing under a specific stress level and duration without failure can demonstrate certain reliability level. By raising the stress level and shortening the duration, time and testing costs may be saved without lowering the intended reliability level. Other applications of the load enhancement factor involves back calculating the reliability level for a given value of Load Enhancement Factor (LEF) and duration, or back calculating the duration for a given value of LEF and reliability level. These two back calculations are used to assess and compare existing or new test programs.

FIG. 1 is a flow diagram illustrating steps for executing a method of determining a LEF according to an embodiment. The method steps include starting the analysis by verifying completion of testing at method step 120 and retrieval of data from a database 100 at method step 150. The retrieved data or information from database 100 may include, but is not limited to, coupon level testing results from tests run on subject composite coupons, time stamp information, test item identification. The coupon testing may be conducted in any manner that is appropriate to developing the necessary data set. Variables that may be incorporated in the grouping of the data can include, but are certainly not limited to, stress levels, life cycles, environmental conditions, coupon size, coupon shape, coupon manufacturing process, and similar variables.

An analysis of the data is performed, determining whether the coupon level testing was conducted with a single stress value or whether multiple stress levels were tested at method step 200. If a single stress value was tested, the flow chart proceeds in the negative to step 420 and progresses therefrom. If multiple stress values were tested, the flow chart proceeds in the affirmative to step 430 and proceeds therefrom. Although the example shown in FIG. 1. utilizes the Weibull statistical distribution model, similar analytic steps may be used to analyze data fitting different distribution models, including but not limited to the normal statistical distribution and similar statistical distributions. Adjustment of the equations is hereby contemplated to accommodate such distribution models to accommodate scatter and the other variables contemplated above in the coupon testing or other data stored on the database 100 and such further developments are within the spirit of the various embodiments.

Figure 3A:
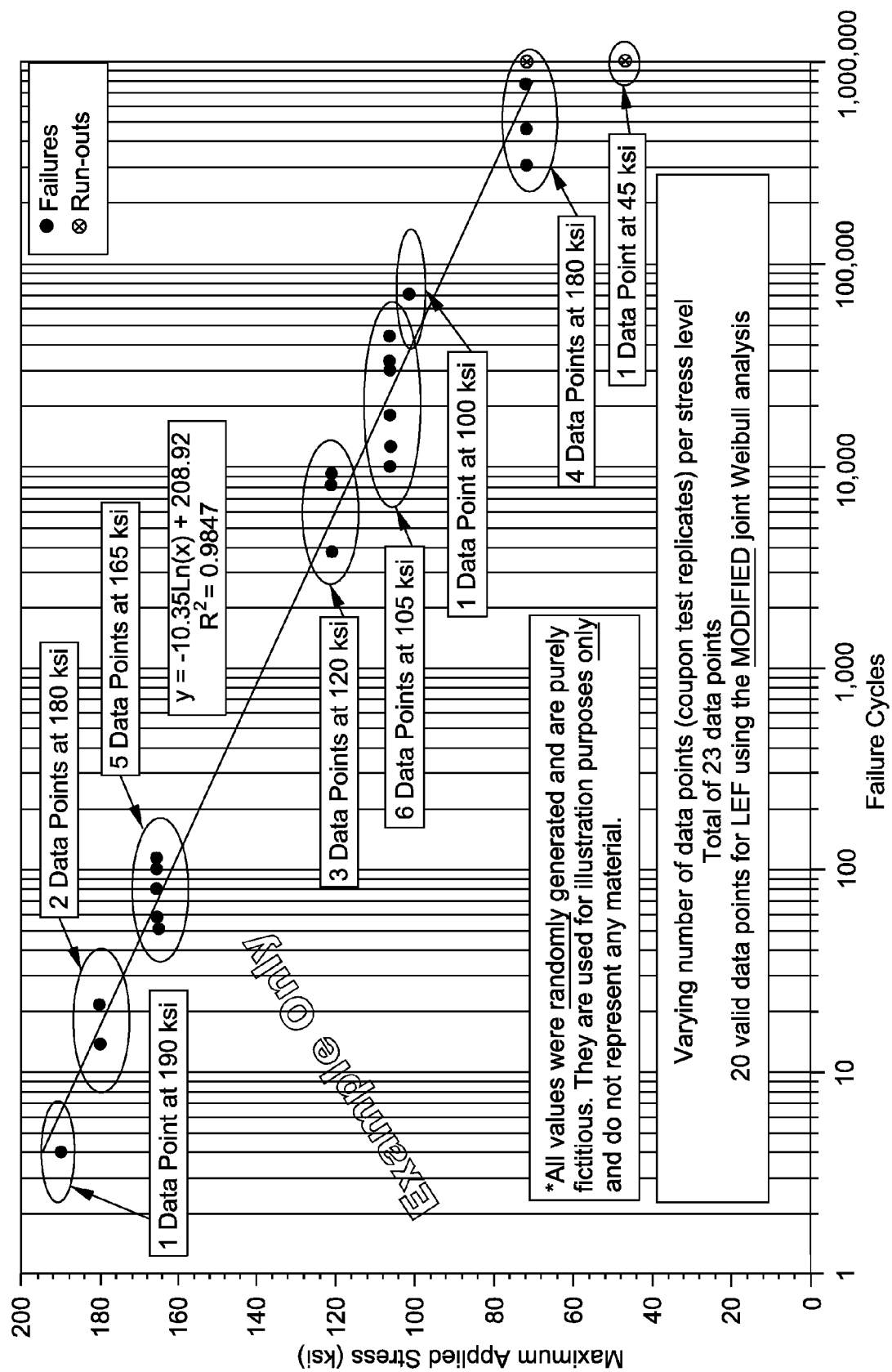
FIG. 3A is a graph illustrating a hypothetical S-N curve with a distribution of data points suitable for use by an embodiment.
Figure 3B:
FIG. 3B is a table comparing the features of a Load Enhancement Factor (LEF) approach to fatigue testing developed by the Naval Air Development Center (NADC)-Northrop to an LEF approach to fatigue testing as disclosed herein.
Figure 4:
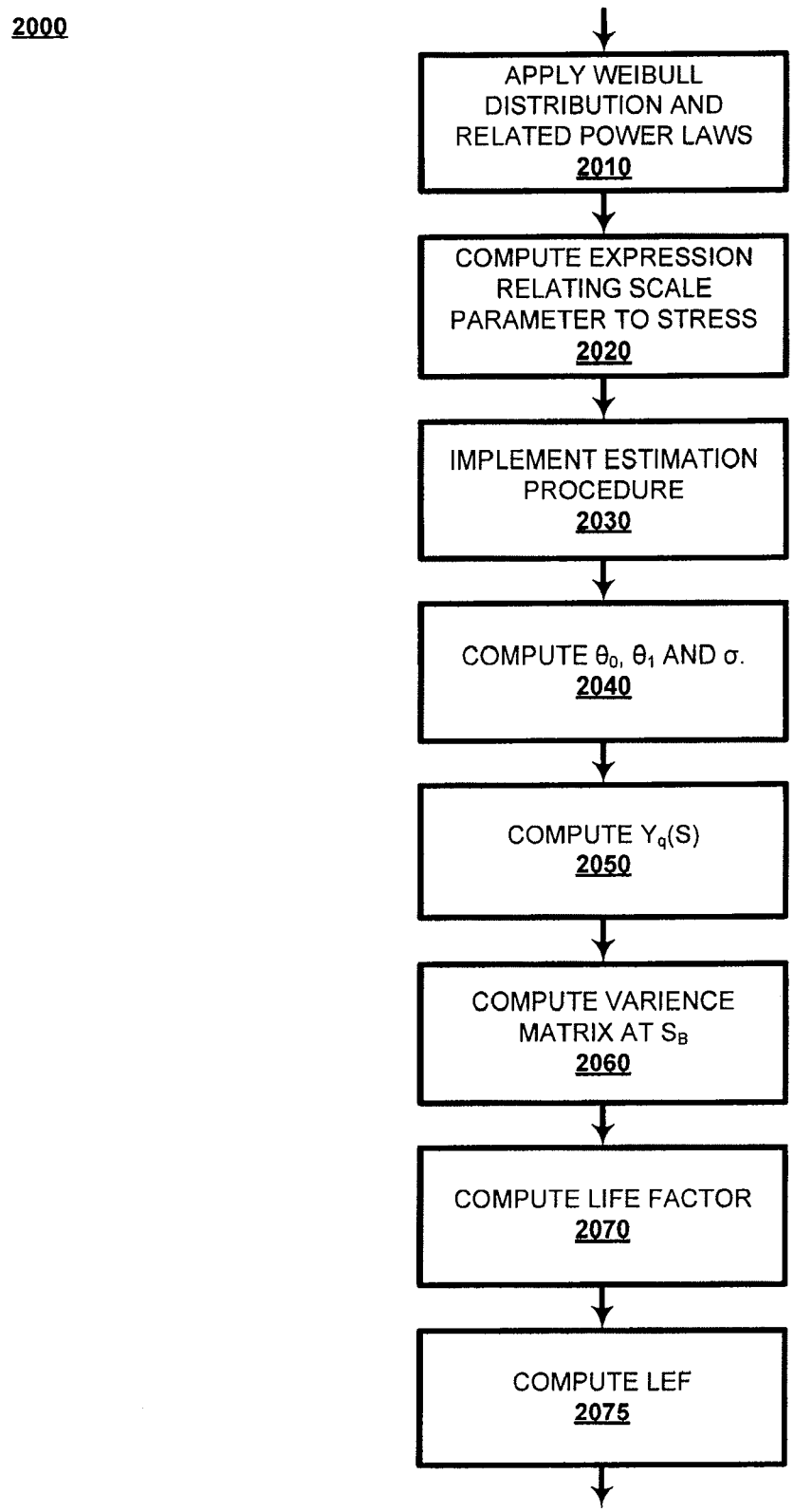
FIG. 4 is a flow diagram illustrating steps for performing a Weibull Regression Analysis segment according to another embodiment.
Figure 5:
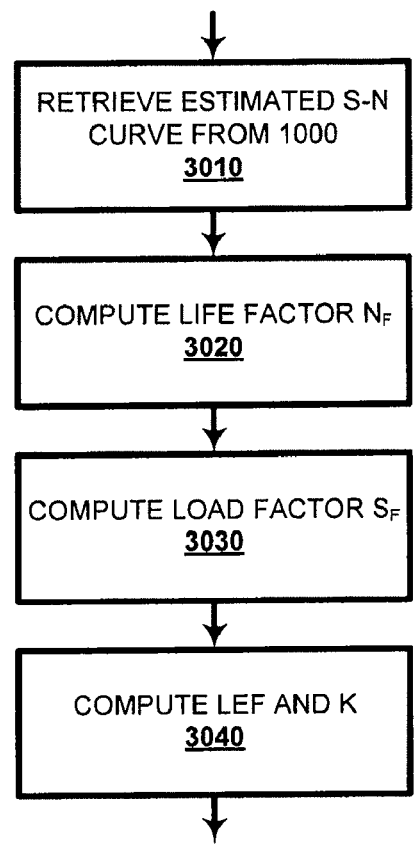
FIG. 5 is a flow diagram illustrating steps for performing a coupon testing segment according to an embodiment.

In the case of a single stress value being tested, the Joint Weibull code segment 1000, see for instance FIG. 3A, may be applied alone or in combination with the Weibull regression code segment 2000, see for instance FIG. 4, depending on the analysis of the data, to determine a Load Enhancement Factor (LEF). In method step 420 and 430, a Weibull distribution is assumed and determination of sufficient failure data is carried out. The next determination is made in method step 440 whether sufficient runout data points exist in the data set from database 100. If the runout data is insufficient, then the method proceeds in the negative and ends.

If sufficient runout data exists, then the method proceeds in the affirmative to method step 460. At method step 460, a determination is made whether the data on static strength in the coupon testing is included. If the static data is not used, the method continues in the negative to the Modified Joint Weibull Analysis code segment 1000 and continues computations through this methodology only. If static strength data is used here only to aid the Weibull regression approach because of only single stress data. The method continues to the Weibull Regression Analysis code segment 2000. It is understood that the computer can attempt to compute an LEF value for both cases or elect to compute using a single method. The results are displayed in method step 500. The user may then elect to use the LEF that, to the best engineering judgment of the user, that best fits the goals of the investigation.

The determination of which LEF value to utilize is, in this case, left to the best engineering judgment of the user. This engineering judgment may be based on the type of data available and additional factors that may include, but certainly are not limited to, the type of composite material, the operational environment of the material, the configuration of the composite material, the manufacturing process of the composite material, the testing being conducted at the component level on the material, and similar variables. It is also understood that a further logic may be added to exclude one or the other of the computations based on further qualitative inputs from the user that would typify such factors.

If multiple stress values were tested, the flow chart proceeds at step 200 in the positive to step 430. In method step 430, the Weibull distribution is assumed. A determination is made in method step 430 if a single replicate was tested or multiple replicates were tested in the test data retrieved in step 150 from database 100. If a single replicate was tested, the method proceeds in the affirmative at step 450 to determine if there are sufficient run-out in each stress level. The method proceeds to the Weibull Regression code segment 2000 if there are single replicate per stress level and multiple stress level. The method proceeds to computer LEF after fitting the Weibull regression model. The LEF computation is then output to the user in method step 500.

If multiple replicates were tested in the test data retrieved in step 150 from database 100, then the method proceeds to steps 440 and 450 when there are enough failure and run-outs at multiple stress level. Both the Modified Joint Weibull Analysis and Weibull regression model would be implemented, and LEF from both approaches would be reported in step 500. The user may then elect to use the LEF that, to the best engineering judgment of the user, that best fits the goals of the investigation.

The determination of which LEF value to utilize is, in this case, left to the best engineering judgment of the user. This engineering judgment may be based on the type of data available and additional factors that may include, but certainly are not limited to, the type of composite material, the operational environment of the material, the configuration of the composite material, the manufacturing process of the composite material, the testing being conducted at the component level on the material, and similar variables. It is also understood that a further logic may be added to exclude one or the other of the computations based on further qualitative inputs from the user that would typify such factors.

As noted, the primary drawbacks of using the Whitehead, Vol. I traditional LEF computation approach described earlier included the limitation that requires an equal number of coupon replicates be tested at every stress level and the further requirement that an equal number of replicates survive to run-out at every stress level. The Modified Joint Weibull Analysis and Weibull Regression methods presented herein overcomes, at least, these limitation. It allows for the analysis of the data derived from coupon testing to determine what scenario best suits the data and applying the code segment for Modified Joint Weibull Analysis, the code segment for Weibull Regression, or both code segments.

Figure 2:
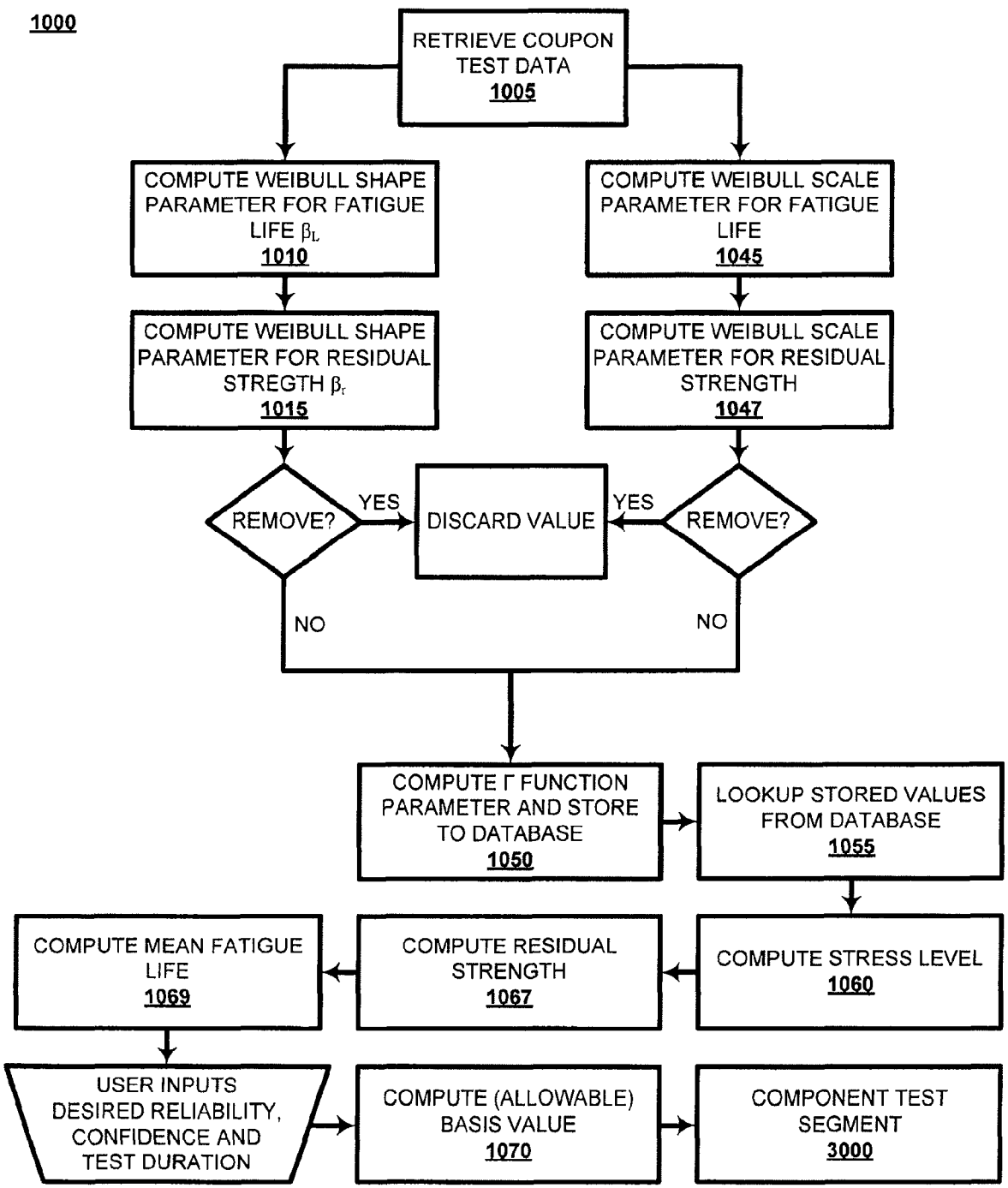
FIG. 2 is a flow diagram illustrating steps for performing a Modified Joint Weibull Analysis segment according to an embodiment.

FIG. 2 shows a flow chart for the method of calculating LEF in a Modified Joint Weibull Analysis. The methodology uses a Modified Joint Weibull Analysis. The Modified Joint Weibull Analysis allows for the use of data derived from an unequal number of coupon replicates that are tested within a variety of stress levels in method step 1020, as shown in FIG. 2. The data from the coupon testing code segment 1010 utilizes testing of coupons to define Weibull parameters. The Modified Joint Weibull analysis presented here is versatile and more robust than the traditional method described in Whitehead et al. reports, providing the freedom to run as few or as many test replicates within each stress level as deemed necessary. The foundation to formulate the approach remains the same as that used by the traditional LEF method, however significant improvements are made to facilitate the inclusion of scatter and residual strength in calculating the LEF, thus overcoming the shortfalls of the traditional method.

The method may utilize various data points and values develop and stored from the coupon-level testing segment 1010 for each configuration type under investigation. This data and values can include, but are not limited to: Weibull shape parameters for both fatigue life and residual strength; Weibull scale parameters for both fatigue life and residual strength; and Stress-Life relationships in the form of S-N curves.

To compute the Weibull shape parameter for fatigue life, ( ) the equation for the Modified Joint Weibull analysis uses EQ-1 in method step 1010, $$\sum_{i=1}^{M}\left(n_{fi}\frac{\sum_{j=1}^{n_i}X_{ij}^{\beta_L}\ln(X_{ij})}{\sum_{j=1}^{n_i}X_{ij}^{\beta_L}}\right)-\sum_{i=1}^{M}\frac{n_{fi}}{\beta_L}-\sum_{i=1}^{M}\sum_{j=1}^{n_{fi}}\ln(X_{ij})=0 \qquad (EQ\text{-}1)$$

Note that $n_{f_i}$ does not equal $n_i$ since some of $n_i$ coupons may survive to "run-out."

To compute the Weibull shape parameter for residual strength, ($\beta_r$), the method uses equation EQ-2, similar to equation EQ-1, in method step 1015 and $n_{r_i}$ is used for the Modified Joint Weibull analysis and becomes, $$\sum_{i=1}^{M}\left(n_{r_i}\frac{\sum_{j=1}^{n_i}W_{ij}^{\beta_r}\ln(W_{ij})}{\sum_{j=1}^{n_i}W_{ij}^{\beta_r}}\right)-\sum_{i=1}^{M}\frac{n_{r_i}}{\beta_r}-\sum_{i=1}^{M}\sum_{j=1}^{n_i}\ln(W_{ij})=0 \qquad (EQ\text{-}2)$$

Noting that $n_{r_i}$ represents the number of coupons undergoing residual strength tests. These are the "run-out" coupons from the $i^{th}$ group (stress level). The Weibull shape parameter for static strength, ($\beta_s$), is computed in equation EQ-3 an analogous manner at step 1017, namely, $$n_s\frac{\sum_{j=1}^{n_s}S_j^{\beta_s}\ln(S_j)}{\sum_{j=1}^{n_s}S_j^{\beta_s}}-\frac{n_s}{\beta_s}-\sum_{j=1}^{n_s}\ln(S_j)=0 \qquad (EQ\text{-}3)$$

These equations must be solved using an iterative approach. Generally, the higher the shape parameter, the less variability a material exhibits.

Note that these equations for the Modified Joint Weibull analysis are different from those presented by the traditional LEF method. Specifically, these equations, in conjunction with the computations that follow, overcome the requirements that an equal number of coupon replicates be tested at every stress level and that an equal number of replicates survive to run-out at every stress level. They do not simply account for a simple statistical average, as noted above regarding the traditional method of calculating LEF. Instead, the Modified Joint Weibull Analysis equations accommodate scatter in the data throughout the tested groups, regardless of the presence of equal numbers of tested coupon replicates.

The relevant equations allow an unequal number of coupon replicates to be tested within each stress level, allowing the computation to quantify and utilize scatter within the residual strength testing and data. The accommodation of scatter is evident from the test data developed in method step 1010. A sample of an S-N curve is shown in FIG. 3A. The S-N curve is shown using hypothetical values as an example of the results contemplated by the iterative approach employed on the equations EQ-1 through EQ-3. The analysis presented by the traditional method, if analyzing the hypothetical data points of FIG. 3A, would allow for consideration of a maximum of 6 data points to be used (at a stress level of 105 thousand pounds per square inch ("ksi")). By comparison, the modified equations EQ-1 through EQ-3 would allow 20 data points comprising data from a variety of stress levels. Note that stress levels containing only one coupon replicate data point cannot be utilized to quantify scatter.

After both shape parameters have been computed, the scale parameters can then be determined in method step 1045. Since a unique scale parameter exists for each stress level, there will be, at most, M scale parameters for both fatigue life and residual strength. By definition, each of the scale parameters represents the value at which 63.2% of all data points should fall below. For example, suppose the life scale parameter for a particular stress level is $\alpha_L$=567,890 cycles. This implies that approximately 63.2% of the coupons tested at this stress level will fail prior to reaching 567,890 cycles. Similarly, suppose the scale parameter for residual strength for a particular stress level is $\alpha_r$=58.3 ksi. This equates to about 63.2% of the coupons that are tested for residual strength will have a residual strength less than 58.3 ksi.

The life scale parameter for each stress level ($i^{th}$ group) is computed using equation EQ-4 in step 1045, $$\alpha_{L_i} = \left[\frac{1}{n_{f_i}} \sum_{j=1}^{n_i} X_{ij}^{\beta_L}\right]^{\frac{1}{\beta_L}} \tag{EQ-4}$$

While the scale parameter for residual strength for each stress level ($i^{th}$ group) is computed using equation EQ-5 in step 1047, $$\alpha_{r_i} = \left[\frac{1}{n_{r_i}} \sum_{j=1}^{n_i} W_{ij}^{\beta_r}\right]^{\frac{1}{\beta_r}} \tag{EQ-5}$$

Similarly, the scale parameter for static strength can be computed in equation EQ-6 in step 1049, $$\alpha_s = \left[\frac{1}{n_s} \sum_{j=1}^{n_s} S_j^{\beta_s}\right]^{\frac{1}{\beta_s}} \tag{EQ-6}$$

Once the shape and scale parameters have been established in equations EQ-1-EQ-6, values for the Chi-squared distribution and Gamma functions may be obtained. The value of the Chi-squared distribution establishing γ level of confidence is, $\chi_{\gamma,2n_L}^2$, where $2n_L$ are the degrees of freedom corresponding to coupon-level testing.

The equation used to compute the value of the Gamma function for the life shape parameter is provided in equation EQ-1 and computed in step 1050, $$\Gamma\left[\left(\frac{\beta_L + 1}{\beta_L}\right)\right] \tag{EQ-7}$$

Values of the Gamma function are computed for varying life shape parameters can be computed and stored in a database in, for example, a series of tables. Method step 1055 includes a lookup step, wherein the value of the gamma function is determined from those stored in a table. Similarly, the equation used to compute the value of the Gamma function for the residual strength shape parameter is provided as EQ-8, $$\Gamma\left[\left(\frac{\beta_r + 1}{\beta_r}\right)\right] \tag{EQ-8}$$

Values of the Gamma function are computed for varying residual strength shape parameters are similarly stored and the method step 1055 also provides for a lookup of the gamma value.

Likewise, the mean static strength is computed, the mean residual strength at the stress level, and mean fatigue life at the $i^{th}$ stress level are computed, the mean static strength being computed in step 1060 using EQ-9, $$S_M = \alpha_s \Gamma\left[\left(\frac{\beta_s + 1}{\beta_s}\right)\right] \tag{EQ-9}$$

the mean residual strength at the $i^{th}$ stress level being computed at step 1065 using EQ-10, $$P_{T_i} = \alpha_{r_i} \Gamma\left[\left(\frac{\beta_r + 1}{\beta_r}\right)\right] \tag{EQ-10}$$

the mean fatigue life at the $i^{th}$ stress level being computed at step 1069 using equation EQ-11, $$N_{M_i} = \alpha_{L_i} \Gamma\left[\left(\frac{\beta_L + 1}{\beta_L}\right)\right] \tag{EQ-11}$$

Similarly, the design life at a desired reliability (R) and the residual strength allowable at a desired reliability (R) for the $i^{th}$ stress level are computed in method step 1070 using equations EQ-12 and EQ-13, respectively, where EQ-12 is used in step 1070 to compute the design life at the desired reliability, $$N_i = \alpha_{L_i} \left[\frac{[-\ln(R)]}{\frac{\chi_{\gamma,2n_L}^2}{2n_L}}\right]^{\frac{1}{\beta_L}} \tag{EQ-12}$$

Note that the sample size in the denominator refers to the total number of coupons tested in fatigue. This accounts for both failures and run-outs, since these lives are still considered valid data points.

The residual strength allowable at desired reliability (R) for the $i^{th}$ stress level is computed in step 1070 using EQ-13, $$W_{r_i} = \alpha_{r_i} \left[ \frac{[-\ln(R)]}{\frac{\chi^2_{\gamma, 2n_r}}{2n_r}} \right]^{\frac{1}{\beta_r}} \quad \text{(EQ-13)}$$

The static strength allowable at desired reliability (R) is computed in claim 1060 using equation EQ-14, $$S_r = \alpha_s \left[ \frac{[-\ln(R)]}{\frac{\chi^2_{\gamma, 2n_s}}{2n_s}} \right]^{\frac{1}{\beta_s}} \quad \text{(EQ-14)}$$

Note that the sample size in the denominator refers to the total number of coupons reaching the run-out condition. Since residual allowable only pertains to residual strength, only the coupons reaching run-out are counted in the sample size.

The method proceeds to utilize the test results of method step 1010-1070, which generates additional data to be stored on the database 100, to determine the Weibull shape and scale parameters based on the coupon-level testing data returned in steps 1020-1070. A further method step represented by a code segment 3000 applies the Weibull shape parameters to generate an S-N curve for use in computing the Load Enhancement Factor (LEF) for component level testing in step/code segment 3000.

Since these equations require the fatigue life of the component to be defined in terms of the number of lifetimes, the definition of 1 lifetime must be equated to a corresponding cycle count, $X_1$. If the traditional LEF approach is used, note that the static strength values will not be considered in the statistical analysis, whereas the method presented in Section 2000 will utilize the static data.

The stress level on the Mean S-N curve that corresponds to 1 lifetime, $(S_1)$, is the applied stress that can be used in the component fatigue test to achieve the desired levels of reliability and confidence. Equivalently, the component test may run at a stress level of $S_2$ for a duration equal to the Life Factor multiplied by 1 lifetime. The resulting duration is equal to the Life Factor. Mathematically, the Life Factor is defined by EQ-15 and computed in step 3020, $$N_F = \frac{\Gamma\left(\frac{\beta_L + 1}{\beta_L}\right)}{\left[\frac{-\ln(R)}{\frac{\chi^2_{\gamma, 2n_0}}{2n_0}}\right]^{\frac{1}{\beta_L}}} \quad \text{(EQ-15)}$$

Refer to method step 1050 in FIG. 2 for the values of the Chi-Squared distribution. Note that the sample size $n_0$ being used now corresponds to the number of fatigue tests planned at the component level, not the coupon level.

If a large number of replicates are tested on the coupon-level, it is reasonable to assume that the Weibull shape parameters accurately quantify the fatigue scatter and these values are inherent properties of the material. To bridge the gap between coupon- and component-level testing, the sample size in the equations of this code segment must account for the number of component tests since the component sample size also affects the level of reliability. Therefore, the shape parameters are developed using the number of coupon replicates, while the Life, Load, and Load Enhancement Factors computed in the Modified Joint Weibull Analysis component testing code segment 3000 rely on the number of components tested.

The Load Factor, $(S_F)$, is then computed by EQ-16 in method step 3030 and is represented as, $$S_F = \frac{[K(N_0)]\Gamma\left(\frac{\beta_r + 1}{\beta_r}\right)}{\left[\frac{-\ln(R)}{\frac{\chi^2_{\gamma, 2n_0}}{2n_0}}\right]^{\frac{1}{\beta_r}}} \quad \text{(EQ-16)}$$

Where the scaling coefficient, $[K(N_0)]$, is defined as, $$[K(N_0)] = \frac{\left[\Gamma\left(\frac{\beta_L + 1}{\beta_L}\right)\right]^{\frac{\beta_L}{\beta_r}}}{\Gamma\left(\frac{\beta_r + 1}{\beta_r}\right)} \quad \text{(EQ-17)}$$

This scaling coefficient is required to ensure that the test duration equals $N_F$ when the Load Factor, $S_F=1$. Again, the Weibull shape and scale parameters are those previously derived in the Modified Joint Weibull analysis code segment 1000. Note that the Load Factor, $(S_F)$, can only be employed when the planned test duration of the component-level fatigue test is assumed to equal 1 lifetime.

If both the applied loads and duration of the component-level fatigue test are varied, then the Load Enhancement Factor (LEF) may be employed. This factor is computed as equation EQ-18 in method step 2070, $$LEF = \frac{[K(N_0)]\Gamma\left(\frac{\beta_r + 1}{\beta_r}\right)}{\left[\frac{-\ln(R)(N_0)^{\beta_L}}{\frac{\chi^2_{\gamma, 2n_0}}{2n_0}}\right]^{\frac{1}{\beta_r}}} = \left(\frac{N_F}{N_0}\right)^{\left(\frac{\beta_L}{\beta_r}\right)} \quad \text{(EQ-18)}$$

Note that if the test duration is equal to 1 lifetime, $N_0=1$, the Load Enhancement Factor is equal to the Load Factor, $S_F$. Similarly, if the Load Enhancement Factor is equal to 1, solving for the test duration will yield the Life Factor.

The LEF is applied in a similar manner as the Load Factor, with the exception that the test duration must be specified. Whereas the Load Factor is associated with a duration equal to 1 lifetime, a Load Enhancement Factor uses a test duration that is not necessarily equal to 1 lifetime. In lieu of using a duration of 1 lifetime and increasing the loads by a finite percentage, an infinite number of equivalent combinations are possible by using the Load Enhancement Factor.

If the Modified Joint Weibull analysis will be used to analyze fatigue data, it is necessary that at least two coupon replicates must be tested per stress level. In addition, at least two coupon replicates from the entire test program must survive to the run-out condition and be tested for residual strength. These items are checked in the flow chart of FIG. 1 in steps 200, 320, 340, and 420. As with the traditional approach to compute Load Enhancement Factors, this modified approach does not account for variability in static strength. The use of scatter in static strength is incorporated in the Weibull Regression analysis method and code segment 2000 presented below.

FIG. 4 is a flow chart of the Weibull Regression analysis segment of a method 2000 according to an embodiment. Given the coupon test data with single stress levels, a Weibull Regression model can be used to estimate the S-N relationship and provide estimates of various quantities associated with the Load Enhancement Factor, as noted in the Whitehead, Vol. II reference and the traditional method for calculating LEF using Weibull Regression modeling. As noted, the Weibull Regression analysis improves on the traditional method and includes accommodation for both single and multiple stress level coupon testing and the method utilizes the static data.

Assuming that there are different fatigue stress levels and a Weibull distribution is appropriate to describe the fatigue failure at each stress level, this Weibull model with different scale parameters can have the following form in equation EQ-19, where $\alpha_i$ is the scale parameter for the $i^{th}$ group, and $\beta_{SN}$ is the common shape parameter, $$f(x_{ij}) = \frac{\beta_{SN}}{\alpha_i}\left(\frac{x_{ij}}{\alpha_i}\right)^{\beta_{SN}-1}\exp\left(-\left(\frac{x_{ij}}{\alpha_i}\right)^{\beta_{SN}}\right) \quad \text{(EQ-19)}$$

where $x_{ij}$ represents the failure cycles for the $j^{th}$ coupon in the $i^{th}$ group. It is conceivable that $a_i$ changes with the fatigue stress level as a covariate.

At step 2010, the Weibull distribution and related power laws is applied. The Weibull regression model representing the power law in the S-N curve would relate the log of the scale parameter with the log of stress level in method step 2020. The underlying relationship may be one of any number of linear or non-linear relationships between the log of the scale parameter and the log of stress level. A non-limiting example is found in a linear relationship between log of the scale parameter and log of stress level, is expressed by equation EQ-20, $$\ln(\alpha_i) = \theta_0 + \theta_1 \ln(S_i) \quad \text{(EQ-20)}$$

The method makes use of the relationship between Weibull and Extreme Value distribution to implement an estimation procedure in method step 2030 Let $y_{ij}=\ln(x_{ij})$.

The probability density function and the cumulative distributions for y are represented in equations EQ-21 and EQ-22, respectively, $$g(y_{ij}) = \frac{1}{\sigma}\exp\left(\frac{y_{ij}-\phi_i}{\sigma} - \exp\left(\frac{y_{ij}-\phi_i}{\sigma}\right)\right) \quad \text{(EQ-21)}$$

$$G(y_{ij}) = 1 - \exp\left(-\exp\left(\frac{y_{ij}-\phi_i}{\sigma}\right)\right) \quad \text{(EQ-22)}$$

where $\phi_i=\theta_0+\theta_1 \ln(S_i)=\ln(\alpha_i)$ and $\sigma=1/\beta_{SN}$. Then, the log likelihood function for Extreme Value distribution with covariate in M groups is defined in equations EQ-23 and EQ-24, $$\ln L = \sum_{i=1}^{M}\sum_{j=1}^{n_i}\delta_{ij}\left(\frac{y_{ij}-\phi_i}{\sigma}-\ln(\sigma)\right) - \sum_{i=1}^{M}\sum_{j=1}^{n_i}\exp\left(\frac{y_{ij}-\phi_i}{\sigma}\right) \quad \text{(EQ-23)}$$

$$\ln L = \sum_{i=1}^{M}\sum_{j=1}^{n_i}\delta_{ij}\left(\frac{y_{ij}-\theta_0-\theta_1\ln(S_i)}{\sigma}-\ln(\sigma)\right) - \sum_{i=1}^{M}\sum_{j=1}^{n_i}\exp\left(\frac{y_{ij}-\theta_0-\theta_1\ln(S_i)}{\sigma}\right) \quad \text{(EQ-24)}$$

where $\delta_{ij}$ is an indicator variable with two values. $\delta_{ij}=1$ when $y_{ij}$ is a failure, and $\delta_{ij}=0$ when $y_{ij}$ is a run-out.

Setting the first partial derivatives of the above expression to zero, one obtains, $$0 = \sum_{i=1}^{M}\sum_{j=1}^{n_i}\frac{-1}{\sigma}\left(\delta_{ij}-\exp\left(\frac{y_{ij}-\theta_0-\theta_1\ln(S_i)}{\sigma}\right)\right) \quad \text{(EQ-25)}$$

$$0 = \sum_{i=1}^{M}\sum_{j=1}^{n_i}\frac{-1}{\sigma}\left(\delta_{ij}\ln(S_i)-\ln(S_i)\exp\left(\frac{y_{ij}-\theta_0-\theta_1\ln(S_i)}{\sigma}\right)\right) \quad \text{(EQ-26)}$$

$$0 = \sum_{i=1}^{M}\sum_{j=1}^{n_i}\frac{-1}{\sigma}\left(\delta_{ij}\left[\frac{y_{ij}-\theta_0-\theta_1\ln(S_i)}{\sigma}+1\right] - \exp\left(\frac{y_{ij}-\theta_0-\theta_1\ln(S_i)}{\sigma}\right)\left(\frac{y_{ij}-\theta_0-\theta_1\ln(S_i)}{\sigma}\right)\right) \quad \text{(EQ-27)}$$

There is no helpful simplification for equations EQ-25 and EQ-26 in terms of $\theta_0$ and $\theta_1$. Hence, solving for $\theta_0$, $\theta_1$, and $\sigma$ requires a numerical algorithm, for example, but not limited to, the Newton-Rhapson method. These parameters are estimated through nonlinear optimization in method step 2040.

Once these parameters are estimated through a nonlinear optimization, the 95% lower confidence limit for the $100q^{th}$ percentile, $Y_q(S)$, is given by equation EQ-28 employed in method step 2050, $$\hat{Y}_q(S) - 1.645\sqrt{V(\hat{Y}_q(S))} \quad \text{(EQ-28)}$$

where the 100 $q^{th}$ percentile estimate at S is $$\hat{Y}_q(S) = \hat{\theta}_0 + \hat{\theta}_1\ln(S) + C_q\hat{\sigma},$$

and its variance is approximated by EQ-29 in method step 2059, $$V(\hat{Y}_q(S)) \approx V(\hat{\theta}_0) + \ln(S)^2 V(\hat{\theta}_1) + C_q^2 V(\hat{\sigma}) + \quad \text{(EQ-29)}$$
$$2\ln(S)\text{Cov}(\hat{\theta}_0, \hat{\theta}_1) + 2C_q\text{Cov}(\hat{\theta}_0, \hat{\sigma}) + 2\ln(S)C_q\text{Cov}(\hat{\theta}_1, \hat{\sigma})$$

where $C_q = \ln(-\ln(1-q))$. The value 1.645 is the $95^{th}$ percentile of a standard normal. This value will change if the confidence level change. The B-basis value is the 95% lower confidence limit in equation EQ-28 with q=0.10, and A-basis with q=0.01. Note that the variance and covariance estimates for these parameters are needed to complete this computation.

The variance and covariance estimates for these parameters are computed in steps 2050-2060 from the elements of the inverse of the observed information matrix ($I_0^{-1}$). In this Extreme Value regression model, the observed information matrix has the form provided in EQ-30, $$I_0 = \begin{bmatrix} -\frac{\partial^2 \ln(L)}{\partial \theta_0 \partial \theta_0} & -\frac{\partial^2 \ln(L)}{\partial \theta_0 \partial \theta_1} & -\frac{\partial^2 \ln(L)}{\partial \theta_0 \partial \sigma} \\ -\frac{\partial^2 \ln(L)}{\partial \theta_0 \partial \theta_1} & -\frac{\partial^2 \ln(L)}{\partial \theta_1 \partial \theta_1} & -\frac{\partial^2 \ln(L)}{\partial \theta_1 \partial \sigma} \\ -\frac{\partial^2 \ln(L)}{\partial \theta_0 \partial \sigma} & -\frac{\partial^2 \ln(L)}{\partial \theta_1 \partial \sigma} & -\frac{\partial^2 \ln(L)}{\partial \sigma \partial \sigma} \end{bmatrix} \quad \text{(EQ-30)}$$

Because the first partial derivatives are zero at the Maximum Likelihood Estimation (MLE), a certain amount of simplification is possible for the information matrix when using this estimation technique. After some algebraic manipulation, it has the following form.

$$I_0 = \frac{1}{\hat{\sigma}^2} \begin{bmatrix} \sum_{i=1}^m n_{f_i} & \sum_{i=1}^m \sum_{j=1}^{n_i} \delta_{ij}\ln(S_i) & \sum_{i=1}^m \sum_{j=1}^{n_i} \delta_{ij}(\hat{z}_{ij}+1) \\ \sum_{i=1}^m \sum_{j=1}^{n_i} \delta_{ij}\ln(S_i) & \sum_{i=1}^m \sum_{j=1}^{n_i} \exp(\hat{z}_{ij})\ln(S_i)^2 & \sum_{i=1}^m \sum_{j=1}^{n_i} \exp(\hat{z}_{ij})\hat{z}_{ij}\ln(S_i) \\ \sum_{i=1}^m \sum_{j=1}^{n_i} \delta_{ij}(\hat{z}_{ij}+1) & \sum_{i=1}^m \sum_{j=1}^{n_i} \exp(\hat{z}_{ij})\hat{z}_{ij}\ln(S_i) & \sum_{i=1}^m \sum_{j=1}^{n_i} (\delta_{ij}+\exp(\hat{z}_{ij})\hat{z}_{ij}^2) \end{bmatrix} \quad \text{(EQ-31)}$$

where $$\hat{z}_{ij} = (y_{ij} - \hat{\theta}_0 - \hat{\theta}_1 \ln(S_i))/\hat{\sigma}.$$

is the inverse of the observed information matrix $$\hat{\Sigma} = I_0^{-1}$$

provided as equation EQ-32 or, $$\hat{\Sigma} = I_0^{-1} = \begin{bmatrix} V(\hat{\theta}_0) & \text{Cov}(\hat{\theta}_0, \hat{\theta}_1) & \text{Cov}(\hat{\theta}_0, \hat{\sigma}) \\ \text{Cov}(\hat{\theta}_0, \hat{\theta}_1) & V(\hat{\theta}_1) & \text{Cov}(\hat{\theta}_1, \hat{\sigma}) \\ \text{Cov}(\hat{\theta}_0, \hat{\sigma}) & \text{Cov}(\hat{\theta}_1, \hat{\sigma}) & V(\hat{\sigma}) \end{bmatrix} \quad \text{(EQ-32)}$$

Note that the B-basis value is a complex function of the stress level through this variance function. It does not have the simple form as the "known" shape parameter under "known" shape parameter scenario. This distinguishes the method of the Weibull Regression model from previously developed methodologies.

However, similar to the method used to develop of Load Enhancement Factor (LEF) under the traditional approach defined in Whitehead et al., LEF is still defined as the ratio of two load values ($S_E$, $S_B$) times a scaling function. LEF is evaluated at $N_0$ lifetime is defined through equation EQ-33, $$LEF(N_0) = \frac{S_E}{S_B} K(N_0) \quad \text{(EQ-33)}$$

Under the Weibull regression model described by equations EQ-19 and EQ-20, noted above, with a linear relationship in log-fatigue stress level, the expected value for fatigue failure cycle at a given stress level (S) is estimated at method step 2030 equation EQ-34 expressed as, $$E(X|S) = \exp(\hat{\theta}_0 + \hat{\theta}_1 \ln(S))\Gamma(1 + 1/\hat{\beta}_{SN}) \quad \text{(EQ-34)}$$

and the B-basis value for fatigue failure cycle at a given stress level, S, is given by equation EQ-35 as, $$B(X|S) = \exp\left[\hat{\theta}_0 + \hat{\theta}_1 \ln(S) + C_{0.10}\hat{\sigma} - 1.645\sqrt{V(\hat{Y}_{0.10}|S)}\right] \quad \text{(EQ-35)}$$

If "one lifetime" is a pre-determined number of cycles derived from past experience on structures and usage, then let $X_1$ be the number of cycles that defines "one lifetime". This can be provided by the user in method step 2050. Then, the method solves for $S_E$ through the E(X|S), and for $S_B$ through the B(X|S), using equations EQ-36 and EQ-37, as $$X_l = E(X|S) = \exp(\hat{\theta}_0 + \hat{\theta}_1 \ln(S))\Gamma(1 + 1/\hat{\beta}_{SN}) \quad \text{(EQ-36)}$$

which leads to an explicit form for $S_E$, $$S_E = \exp\left(\frac{\ln(X_I) - \ln(\Gamma(1 + 1/\hat{\beta}_{SN})) - \hat{\theta}_0}{\hat{\theta}_1}\right) \quad \text{(EQ-37)}$$

To find $S_B$, one would solve for it in equation EQ-38, as $$X_I = \exp\left(\hat{\theta}_0 + \hat{\theta}_1 \ln(S_B) + C_{0.10}\hat{\sigma} - 1.645\sqrt{V(\hat{Y}_{0.10} \mid S_B)}\right) \quad \text{(EQ-38)}$$

Note that the variance estimate involves stress setting. Hence, $S_B$ is found by a nonlinear solver in method step 2060.

Again, following the traditional procedure as outlined in Whitehead Vol. I, the Life Factor is necessary to construct LEF. Life factor is the ratio of the expected failure cycle at $S_B$ and the number of cycles defining one lifetime. The Life Factor described through equation EQ-39, $$N_F = \frac{E(X \mid S_B)}{X_I} = \frac{\exp(\hat{\theta}_0 + \hat{\theta}_1 \ln(S_B))\Gamma(1 + 1/\hat{\beta}_{SN})}{X_I} \quad \text{(EQ-39)}$$

As indicated above, $S_B$ must satisfy the following equation EQ-40, $$X_I = \exp[\hat{\theta}_0 + \hat{\theta}_1 \ln(S_B)]\exp\left[C_{0.10}\hat{\sigma} - 1.645\sqrt{V(\hat{Y}_{0.10} \mid S_B)}\right] \quad \text{(EQ-40)}$$

Therefore, the Life Factor under this Weibull regression approach can be written as equation EQ-41, which is computed in method step 2070, $$N_F = \frac{\Gamma(1 + 1/\hat{\beta}_{SN})}{\exp\left[C_{0.10}\hat{\sigma} - 1.645\sqrt{V(\hat{Y}_{0.10}\mid S_B)}\right]} \quad \text{(EQ-41)}$$

If one chooses to work with A-basis instead of B-basis, one would find $S_A$ by solving equation EQ-420 in place of equation EQ-40, as in method step 2075, $$X_I = \exp\left[\hat{\theta}_0 + \hat{\theta}_1 \ln(S_A) + C_{0.01}\hat{\sigma} - 1.645\sqrt{V(\hat{Y}_{0.01} \mid S_A)}\right] \quad \text{(EQ-42)}$$

In order to determine the scaling function K( ) in equation EQ-33, the same condition is imposed that was imposed from the traditional Weibull Regression analysis approach on LEF, namely, LEF($N_F$)=1. From equation EQ-33, applying this condition yields equation EQ-43, $$K(N_F) = \frac{S_B}{S_E} = \frac{S_B}{\exp[\{\ln(X_I) - \ln(\Gamma(1 + 1/\hat{\beta}_{SN})) - \hat{\theta}_0\}/\hat{\theta}_1]} \quad \text{(EQ-43)}$$

Substituting the definition of $N_F$ in equation EQ-40 into $K(N_F)$ and after some algebraic manipulations, one would obtain equation EQ-44, as $$K(N_F) = (N_F)^{1/\hat{\theta}_1} \quad \text{(EQ-44)}$$

Then, replacing $N_F$ with $N_0$ because they both are relative to $X_1$, the final form of LEF based on Weibull regression has the form of equation EQ-45 in method step 2075, $$LEF(N_0) = \frac{S_E}{S_B}(N_0)^{1/\hat{\theta}_1} = \frac{\exp(-\hat{\theta}_0/\hat{\theta}_1)}{S_B}\left(\frac{X_1 N_0}{\Gamma(1 + 1/\hat{\beta}_{SN})}\right)^{1/\hat{\theta}_1} \quad \text{(EQ-45)}$$

Despite the fact that there is no analytical form for LEF here, it is feasible to compute LEF using equations EQ-40 and EQ-45.

This Weibull Regression model is well documented in the statistical literature. Its application on LEF follows the same general philosophy as in the concept in Whitehead, et al. reference. Whitehead et al. did not use any regression approach in computing LEF, namely they did not make use of the S-N curve at all. Providing that LEF is a scaled ratio of a parameter (expected failure stress) and a parameter estimate (95% lower confidence limit for $10^{th}$ percentile=B-basis). However, the Weibull Regression model used to compute LEF incorporates the S-N relationship through the intercept and slope estimates ($\hat{\theta}_0$, $\hat{\theta}_1$) in the computation. The Weibull Regression model also employs sampling variation through the $V(\hat{Y}_q(S))$ in finding $S_B$, no such variation is accounted for in the traditional LEF method. The definition of one lifetime in fatigue cycles is also explicitly involved. The definition is implicitly used in the traditional LEF methodology. This formulation of LEF in the Weibull Regression method does not involve residual strength. The Weibull Regression method also allows "run-out" and requires multiple stress levels. In addition, the Weibull Regression method does not require multiple replicates per stress level, like its predecessor.

In requiring multiple stress levels, there is at least one exception to this limitation. The Regression Analysis can still be used without multiple stress levels if sufficient static strength data is available, as noted in steps 430 and 450 of FIG. 1. When static test results are available, the method incorporates that into fitting the S-N relationship, essentially drawing the S-N "line". The contribution of static test in the Weibull model relies on several assumptions. These include, but are not limited to, the static strength is the stress level, the cycles to failure is equal to 1, the random scatter of static strength can be ignored, and the failure mode is the same between fatigue cycle failure and static failure. In essence, these static test values would become part of the failure cycle data in estimating the Weibull regression model.

Figure 6:
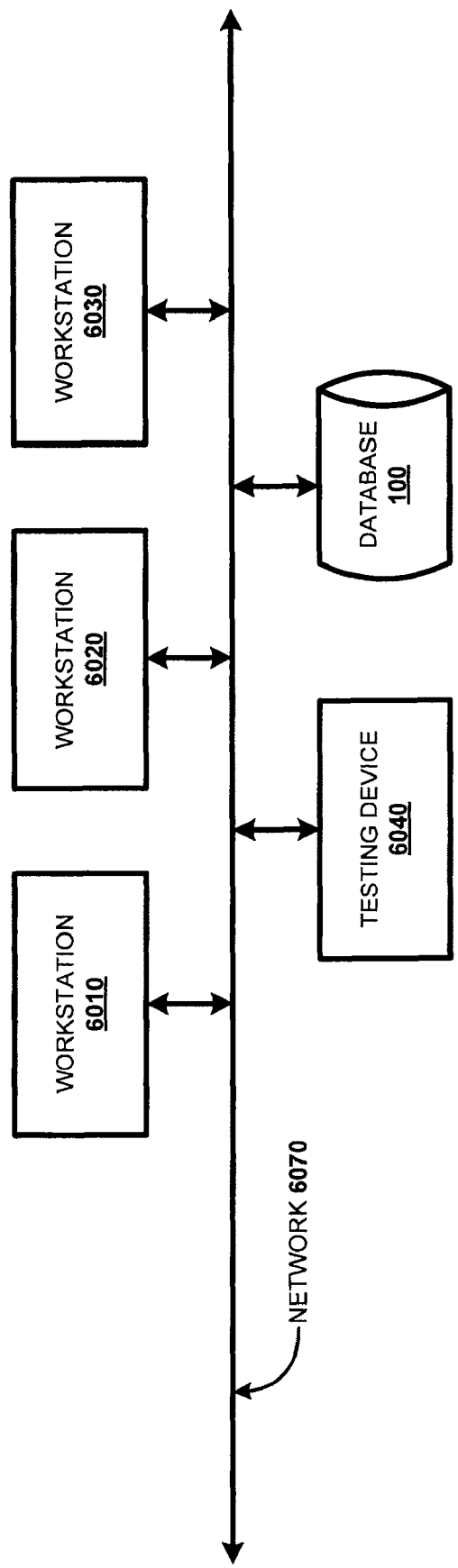
FIG. 6 is a block diagram of a computer network suitable for use with an embodiment.

FIG. 6 is a block diagram of a computer network 6000 in which an embodiment may be implemented. As shown in FIG. 6, the computer network 6000 includes, for example, a server 6010, workstations 6020, and 6030, a material testing device 6040, a database 100, and a network 6070. The network 8070 is configured to provide a communication path for each device of the network 6070 to communicate with the other devices. Additionally, the computer network 6000 may be the Internet, a public switched telephone network, a local area network, private wide area network, wireless network, and the like.

In various embodiments, a method of computing load enhancement factors as described herein may be executed on the server 6010 and/or either or both of the workstations 6020 and 6030. For example, in an embodiment of the disclosure, the server 6010 is configured to execute the method of computing load enhancement factors, provide output for display to the workstations 6020 and/or 6030, and receive input from the database 100, material testing device 6040, workstations 6020 and/or 6030. In various other embodiments, one or both of the workstations 6020 and 6030 may be configured to execute the method of computing load enhancement factors individually or co-operatively.

The material testing device 6040 may be configured to preform coupon and/or component testing and output any suitable results in a computer readable format. Additionally, data associated with coupon testing, component testing, and the like, may be stored on the database 100. The database 100 may additionally be configured to receive and/or forward some or all of the stored data. Moreover, in yet another embodiment, some or all of the computer network 6000 may be subsumed within a single device.

Although FIG. 6 depicts a computer network, it is to be understood that the various embodiments are not limited to operation within a computer network, but rather, the some or all of the embodiments may be practiced in any suitable electronic device. Accordingly, the computer network depicted in FIG. 6 is for illustrative purposes only and thus is not meant to limit the various embodiments in any respect.

The many features and advantages of the various embodiments are apparent from the detailed specification, and thus, it is intended by the appended claims to cover all such features and advantages that fall within the true spirit and scope of these and other embodiments. Further, since numerous modifications and variations will readily occur to those skilled in the art, it is not desired to limit the embodiments to the exact construction and operation illustrated and described, and accordingly, all suitable modifications and equivalents may be resorted to, falling within the scope of the various embodiments.

The invention claimed is:

1. A method of computing at least one of a Load Factor, a Life Factor and a Load Enhancement Factor using Modified Joint Weibull Analysis, comprising the steps of:
   retrieving a test data set from at least one database;
   analyzing the retrieved test data of the test data set for fit with a Weibull distribution model for the test data;
   analyzing the retrieved test data to determine if at least two coupons have been tested and if applied loads and duration of testing at a component-level were varied;
   computing at least one shape parameter for the Weibull distribution model and storing the at least one shape parameter;
   computing at least one scale parameter for the Weibull distribution model of the test data and storing the at least one scale parameter;
   computing a stress to life cycle relationship accounting for scatter in the test data through the Weibull distribution model of the test data by relating a log of the scale parameter of the Weibull distribution model with a log of a stress level of a stress to life cycle relationship; and
   computing, using a processor, the at least one of a Life Factor, a Load Factor and a Load Enhancement Factor as a function of a slope and an intercept of the computed stress to life cycle relationship, thereby accounting for scatter in the at least one Life Factor, a Load Factor and a Load Enhancement Factor.

2. The method of claim 1, wherein the step of computing at least one shape parameter further comprises computing the Weibull shape parameter value for fatigue life, ($\beta_L$), using the equation $$\sum_{i=1}^{M} \left( n_{f_i} \frac{\sum_{j=1}^{n_i} X_{ij}^{\beta_L} \ln(X_{ij})}{\sum_{j=1}^{n_i} X_{ij}^{\beta_L}} \right) - \sum_{i=1}^{M} \frac{n_{f_i}}{\beta_L} - \sum_{i=1}^{M} \sum_{j=1}^{n_{f_i}} \ln(X_{ij}) = 0$$

wherein:
i represents a Group number corresponding to a stress level for coupon-level testing;
M represents a total number of groups for coupon-level testing;
$n_i$ represents a number of coupons in an $i^{th}$ group;
$n_{f_i}$ represents a number of coupons failing in fatigue in the $i^{th}$ group;
j represents a data point element within $i^{th}$ group;
X represents a number of fatigue cycles to failure for a coupon; and
$\beta_L$ represents a shape parameter of a Weibull model for fatigue life measured from coupon-level testing.

3. The method of claim 2, wherein the step of computing at least one shape parameter further comprises computing the Weibull shape parameter value for residual strength, ($\beta_r$), using the equation $$\sum_{i=1}^{M} \left( n_{r_i} \frac{\sum_{j=1}^{n_i} W_{ij}^{\beta_r} \ln(W_{ij})}{\sum_{j=1}^{n_i} W_{ij}^{\beta_r}} \right) - \sum_{i=1}^{M} \frac{n_{r_i}}{\beta_r} - \sum_{i=1}^{M} \sum_{j=1}^{n_{r_i}} \ln(W_{ij}) = 0$$

wherein:
W represents a residual strength at X run-out cycle and stress S;
$n_{r_i}$ represents the number of coupons used in the Weibull model for residual strength in the $i^{th}$ group; and
$\beta_r$ represents a shape parameter of the Weibull model for residual strength measured from coupon-level testing.

4. The method of claim 3, wherein the step of computing at least one shape parameter further comprises computing the Weibull shape parameter value for static strength, ($\beta_s$), is computed in equation $$n_s \frac{\sum_{j=1}^{n_s} S_j^{\beta_s} \ln(S_j)}{\sum_{j=1}^{n_s} S_j^{\beta_s}} - \frac{n_s}{\beta_s} - \sum_{j=1}^{n_s} \ln(S_j) = 0$$

wherein:
$\beta_s$ represents a shape parameter of the Weibull model for static strength measured from coupon-level testing;
$n_s$ represents a number of coupons tested for static strength; and
$S_j$ represents a static strength of j data point for coupon-level testing.

5. The method of claim 4, wherein the step of computing at least one shape parameter further comprises solving for the Weibull shape parameter for static strength, Weibull shape parameter for residual strength, and Weibull shape parameter for fatigue life values for equations using an iterative approach.

6. The method of claim 5, wherein the step of computing at least one scale parameter further comprises calculating the Weibull life scale parameter for each stress level using equation $$\alpha_{L_i} = \left[ \frac{1}{n_{f_i}} \sum_{j=1}^{n_i} X_{ij}^{\beta_L} \right]^{\frac{1}{\beta_L}}$$

wherein:
$\alpha_{L_i}$ represents a scale parameter of the Weibull model for fatigue life measured from coupon-level testing for $i^{th}$ group.

7. The method of claim 6, wherein the step of computing at least one scale parameter further comprises calculating the Weibull scale parameter for residual strength using equation $$\alpha_{r_i} = \left[ \frac{1}{n_{r_i}} \sum_{j=1}^{n_i} W_{ij}^{\beta_r} \right]^{\frac{1}{\beta_r}}$$

wherein:
$\alpha_{r_i}$ represents the scale parameter of the Weibull model for residual strength measured from coupon-level testing for the $i^{th}$ group (stress level).

8. The method of claim 7, wherein the step of computing at least one scale parameter further comprises calculating scale parameter for static strength using equation $$\alpha_s = \left[ \frac{1}{n_s} \sum_{j=1}^{n_s} S_j^{\beta_s} \right]^{\frac{1}{\beta_s}}$$

wherein:
$\alpha_s$ represents the scale parameter of the Weibull model for static strength measured from coupon-level testing.

9. The method of claim 1, wherein the step of computing a stress to life cycle relationship accounting for scatter further comprises obtaining values for Chi-squared distribution and Gamma functions.

10. The method of claim 9, wherein the step of computing a stress to life cycle relationship accounting for scatter further comprises the step of obtaining user input for a desired confidence level ($\gamma$), calculating the value of the Chi-squared distribution for the obtained level of confidence ($\chi^2_{\gamma, 2n_L}$) wherein $2n_L$ are the degrees of freedom corresponding to coupon-level test data.

11. The method of claim 10, wherein the step of obtaining values for the Chi-squared distribution and Gamma functions further comprises calculating values of the Gamma function for the life shape parameter using the equation:

$$\Gamma\left[ \left( \frac{\beta_L + 1}{\beta_L} \right) \right]$$

wherein:
$\Gamma$ represents a gamma function; and
$\beta_L$ represents the shape parameter of the Weibull model for fatigue life measured from coupon-level testing.

12. The method of claim 11, wherein the step of obtaining values for the Chi-squared distribution and Gamma functions further comprises calculating the values of the Gamma function for the residual strength shape parameters using the equation:

$$\Gamma\left[ \left( \frac{\beta_r + 1}{\beta_r} \right) \right]$$

wherein:
$\beta_r$ represents the shape parameter of the Weibull model for residual strength measured from coupon-level testing.

13. The method of claim 12, wherein the step of obtaining values for the Chi-squared distribution and Gamma functions further comprises storing values for the Gamma function for varying shape parameters in a database of Gamma function values.

14. The method of claim 13, wherein the step of obtaining values for the Chi-squared distribution and Gamma functions further comprises a lookup step, wherein the value of the chi square and gamma functions are determined by the lookup step in a table of stored values in the database.

15. The method of claim 14, wherein the step of computing a stress to life cycle relationship accounting for scatter further comprises, calculating mean static strength using the equation:

$$S_M = \alpha_s \Gamma\left[ \left( \frac{\beta_s + 1}{\beta_s} \right) \right]$$

wherein:
$S_M$ represents mean static strength;
$\alpha_s$ represents a scale parameter of a Weibull model for static strength measured from coupon-level testing; and
$\beta_s$ represents a shape parameter of the Weibull model for static strength measured from coupon-level testing.

16. The method of claim 15, wherein the step of computing a stress to life cycle relationship accounting for scatter further comprises calculating mean residual strength using the equation:

$$P_{T_i} = \alpha_{r_i} \Gamma\left[ \left( \frac{\beta_r + 1}{\beta_r} \right) \right]$$

wherein:
$P_{T_i}$ represents a mean residual strength per stress level;
$\alpha_{r_i}$ represents the scale parameter of the Weibull model for residual strength measured from coupon-level testing for the $i^{th}$ group.

17. The method of claim 16, wherein the step of computing a stress to life cycle relationship accounting for scatter further comprises calculating mean fatigue life using equation:

$$N_{M_i} = \alpha_{L_i} \Gamma\left[ \left( \frac{\beta_L + 1}{\beta_L} \right) \right]$$

wherein:

$N_{M_i} = E(X/S)$ represents the mean life for each stress level for coupon-level testing;

$\alpha_{Li}$ represents the scale parameter of the Weibull model for fatigue life measured from coupon-level testing for the $i^{th}$ group.

18. The method of claim 17, wherein the step of computing a stress to life cycle relationship accounting for scatter further comprises obtaining a reliability rating and calculating the design life at a desired reliability and the residual strength allowable at the reliability computed using the equations:

$$N_i = \alpha_{L_i}\left[\frac{[-\ln(R)]}{\frac{\chi^2_{\gamma, 2n_L}}{2n_L}}\right]^{\frac{1}{\beta_L}} \text{ and}$$

$$W_{r_i} = \alpha_{r_i}\left[\frac{[-\ln(R)]}{\frac{\chi^2_{\gamma, 2n_r}}{2n_r}}\right]^{\frac{1}{\beta_r}}$$

wherein:

$N_i$ represents a design life at a desired reliability for the $i^{th}$ stress level;

R represents a reliability function;

$\chi^2_{\gamma,\nu}$ represents a Chi-square random variable with $\gamma$ confidence level and $\nu$ degrees of freedom;

$n_L$ represents a total number of coupons used in a Weibull model for fatigue life cycle; and $n_r$ represents a total number of coupons used in the Weibull model for residual strength.

19. The method of claim 18, wherein the step of computing a stress to life cycle relationship accounting for scatter further comprises calculating static strength allowable at the reliability using the equation:

$$S_r = \alpha_s \left[\frac{[-\ln(R)]}{\frac{\chi^2_{\gamma, 2n_s}}{2n_s}}\right]^{\frac{1}{\beta_s}}$$

and the sample size in the denominator refers to the total number of coupons reaching the run-out condition;

wherein:

$S_r$ represents the static strength allowable;

$n_s$ represents a number of coupons tested for static strength;

$\alpha_s$ represents the scale parameter of the Weibull model for static strength measured from coupon-level testing.

20. The method of claim 19, wherein the step of computing at least one of a Life Factor, a Load Factor and a Load Enhancement Factor further comprises the step of computing the Life Factor using the equation:

$$N_F = \frac{\Gamma\left(\frac{\beta_L + 1}{\beta_L}\right)}{\left[\frac{-\ln(R)}{\frac{\chi^2_{\gamma, 2n_0}}{2n_0}}\right]^{\frac{1}{\beta_s}}}$$

wherein the stored values of the Chi-Squared distribution are retrieved from a database of Gamma function values and the sample size being used corresponds to the number of fatigue tests planned on a component level;

wherein:

$N_F$ represents the Life Factor; and $n_0$ represents a number of component-level tests.

21. The method of claim 20, wherein the step of computing at least one of a Life Factor, a Load Factor and a Load Enhancement Factor further comprises the step of computing the Load Factor, ($S_F$) using the equation:

$$S_F = \frac{[K(N_0)]\Gamma\left(\frac{\beta_r + 1}{\beta_r}\right)}{\left[\frac{-\ln(R)}{\frac{\chi^2_{\gamma, 2n_0}}{2n_0}}\right]^{\frac{1}{\beta_r}}}$$

wherein the scaling coefficient, $[K(N_0)]$, is computed in the form, $$[K(N_0)] = \frac{\left[\Gamma\left(\frac{\beta_L + 1}{\beta_L}\right)\right]^{\frac{\beta_L}{\beta_r}}}{\Gamma\left(\frac{\beta_r + 1}{\beta_r}\right)}$$

wherein:

$S_F$ represents the load factor;

$N_0$ represents a test duration in number of lifetimes.

22. The method of claim 21, wherein the step of computing at least one of a Life Factor, a Load Factor and a Load Enhancement Factor further comprises the step of computing a Load Enhancement Factor using the equation:

$$LEF = \frac{[K(N_0)]\Gamma\left(\frac{\beta_r + 1}{\beta_r}\right)}{\left[\frac{-\ln(R)(N_0)^{\beta_L}}{\frac{\chi^2_{\gamma, 2n_0}}{2n_0}}\right]^{\frac{1}{\beta_r}}} = \left(\frac{N_F}{N_0}\right)^{\left(\frac{\beta_L}{\beta_r}\right)}$$

wherein the scaling coefficient, $[K(N_0)]$, is computed in the form, $$[K(N_0)] = \frac{\left[\Gamma\left(\frac{\beta_L + 1}{\beta_L}\right)\right]^{\frac{\beta_L}{\beta_r}}}{\Gamma\left(\frac{\beta_r + 1}{\beta_r}\right)}$$

wherein:

LEF represents the Load Enhancement Factor.

23. A method of calculating a Load Enhancement Factor for a composite structure using Weibull Regression Analysis, comprising the steps of:

obtaining coupon test data of a material from which the composite structure is formed;

applying a Weibull distribution regression function to the coupon test data to develop an estimated stress to fatigue life curve and applying an equation to relate the log of a scale parameter of the Weibull distribution regression function with the log of a stress level of the stress to fatigue life curve;

implementing an estimation procedure to incorporate a stress to fatigue life relationship in the calculation of the Load Enhancement Factor through an intercept and a slope of the estimates of the stress to fatigue life curve; and specifying, by a user, a confidence level defined in a stress level of a fatigue cycle distribution; and calculating, using a processor, the Load Enhancement Factor using a variance and a co-variance matrix associated with the confidence level and representing the intercept and the slope of the stress to fatigue life curve and developed from the estimation procedure and wherein the Load Enhancement Factor is a scaled ratio of an expected failure stress and the stress level upon which the confidence level is based.

24. The method of claim 23, wherein the coupon test data is from a single stress level.

25. The method of claim 23, wherein the coupon test data is from multiple stress levels and includes static strength data.

26. The method of claim 23, wherein the Weibull distribution regression function is defined by the equation:

$$f(x_{ij}) = \frac{\beta_{SN}}{\alpha_i}\left(\frac{x_{ij}}{\alpha_i}\right)^{\beta_{SN}-1} \exp\left(-\left(\frac{x_{ij}}{\alpha_i}\right)^{\beta_{SN}}\right),$$

wherein:

$\alpha_i$ is the scale parameter for the $i^{th}$ group;

$\beta_{SN}$ is the common shape parameter;

$x_{ij}$ represents the failure cycles for the $j^{th}$ coupon in the $i^{th}$ group.

27. The method of claim 26, wherein the equation to relate the log of a scale parameter of the Weibull distribution regression function with the log of a stress level of the stress to fatigue life curve is a linear relationship between a log of the scale parameter and a log of stress level that is established through the equation:

$$\ln(\alpha_i) = \theta_0 + \theta_1 \ln(S_i),$$

wherein $\alpha_i$ is the scale parameter for the $i^{th}$ group, $\theta_0$ represents the intercept parameter of a Weibull regression model, $\theta_1$ represents the slope parameter of the Weibull regression model, and S represents the stress level applied in fatigue test or static strength for the $i^{th}$ group.

28. The method of claim 27, wherein the step of implementing an estimation procedure further comprises implementing an estimation procedure with $y_{ij}=\ln(x_{ij})$, and where the probability density function and the cumulative distributions for y are computed by equations:

$$g(y_{ij}) = \frac{1}{\sigma}\exp\left(\frac{y_{ij}-\phi_i}{\sigma} - \exp\left(\frac{y_{ij}-\phi_i}{\sigma}\right)\right)$$

$$G(y_{ij}) = 1 - \exp\left(-\exp\left(\frac{y_{ij}-\phi_i}{\sigma}\right)\right)$$

with $\phi_i = \theta_0 + \theta_1 \ln(S_i) = \ln(\alpha_i)$ and $\sigma = 1/\beta_{SN}$ and where the log likelihood function for Extreme Value distribution is expressed with the following equation, with covariate in M groups is described by the equation:

$$\ln L = \sum_{i=1}^{M}\sum_{j=1}^{n_i}\delta_{ij}\left(\frac{y_{ij}-\theta_0-\theta_1\ln(S_i)}{\sigma} - \ln(\sigma)\right) - \sum_{i=1}^{M}\sum_{j=1}^{n_i}\exp\left(\frac{y_{ij}-\theta_0-\theta_1\ln(S_i)}{\sigma}\right),$$

wherein $\delta_{ij}$ is an indicator variable with two values, $\delta_{ij}=1$ when $y_{ij}$ is a failure, and $\delta_{ij}=0$ when $y_{ij}$ is a run-out and where the parameters $\theta_0$ and $\theta_1$ and $\sigma$ are estimated through nonlinear optimization.

29. The method of claim 28, wherein the step of implementing an estimation procedure further comprises computing a variance and a covariance estimate for $\theta_0$, $\theta_1$, and $\sigma$ from the inverse of an observed information matrix, $$\hat{\Sigma} = I_0^{-1},$$

provided by the equation:

$$\hat{\Sigma} = I_0^{-1} = \begin{bmatrix} V(\hat{\theta}_0) & Cov(\hat{\theta}_0,\hat{\theta}_1) & Cov(\hat{\theta}_0,\hat{\sigma}) \\ Cov(\hat{\theta}_0,\hat{\theta}_1) & V(\hat{\theta}_1) & Cov(\hat{\theta}_1,\hat{\sigma}) \\ Cov(\hat{\theta}_0,\hat{\sigma}) & Cov(\hat{\theta}_1,\hat{\sigma}) & V(\hat{\sigma}) \end{bmatrix}$$

wherein:

$I_0^{-1}$ represents the observed information matrix;

V represents a variance;

Cov represents a co-variance;

$\theta_0$ represents an intercept parameter of the Weibull distribution regression function;

$\theta_1$ represents a slope parameter of the Weibull distribution regression function; $\sigma=1/\beta_{SN}$.

30. The method of claim 29, wherein the step of obtaining a confidence level further comprises establishing an A-basis value of a 95% lower confidence limit for the $100q^{th}$ percentile, $Y_q(S)$, using equation:

$$\hat{Y}_q(S) - 1.645\sqrt{V(\hat{Y}_q(S))},$$

wherein the 100 $q^{th}$ percentile estimate at S is $$\hat{Y}_q(S) = \hat{\theta}_0 + \hat{\theta}_1 \ln(S) + C_q\hat{\sigma},$$

and a variance of S is approximated by the expression:

$$V(\hat{Y}_q(S)) \approx V(\hat{\theta}_0) + \ln(S)^2 V(\hat{\theta}_1) + C_q^2 V(\hat{\sigma}) + 2\ln(S)Cov(\hat{\theta}_0,\hat{\theta}_1) + 2C_q Cov(\hat{\theta}_0,\hat{\sigma}) + 2\ln(S)C_q Cov(\hat{\theta}_1,\hat{\sigma}),$$

wherein:

$C_q = \ln(-\ln(1-q))$; and

S represents a stress level applied in a fatigue test $Y_q(S)$ represents a confidence limit at stress S for the $100q^{th}$ percentile.

31. The method of claim 29, wherein the step of obtaining a confidence level further comprises establishing a B-basis value as a 95% lower confidence limit expressed as equation:

$$\hat{Y}_q(S) - 1.645\sqrt{V(\hat{Y}_q(S))}$$

wherein:
1.645 represents a $95^{th}$ percentile of a standard normal.

32. The method of claim 29, further comprising the step of obtaining user input for duration of one lifetime of the composite structure.

33. The method of claim 29, wherein the step of computing the Load Enhancement Factor further comprises evaluating Load Enhancement Factor at $N_0$ lifetime being defined through the equation:

$$LEF(N_0) = \frac{S_E}{S_B} K(N_0)$$

with a linear relationship in log-fatigue stress level and the expected value for fatigue failure cycle at a given stress level (S) being estimated by the equation:

$$E(X|S) = \exp\left[\hat{\theta}_0 + \hat{\theta}_1 \ln(S) + C_{0.10}\hat{\sigma} - 1.645\sqrt{V(\hat{Y}_{0.10}|S)}\right]$$

and the B-basis value for fatigue failure cycle at a given stress level, S, is computed by equation:

$$B(X|S) = \exp\left[\hat{\theta}_0 + \hat{\theta}_1 \ln(S) + C_{0.10}\hat{\sigma} - 1.645\sqrt{V(\hat{Y}_{0.10}|S)}\right]$$

wherein:
E(X/S) represents an expected fatigue failure cycle at stress S;
B(X/S) represents a B-basis value in residual strength at X run-out cycles and stress S;
X represents a number of fatigue cycles to failure for a coupon;
$S_E$ represents a stress level computed from an expected value of fatigue cycle distribution;
$S_B$ represents a stress level computed from a B-basis value of fatigue cycle distribution;
K represents a scaling function for the $N_0$ lifetime;
$\Gamma$ represents a gamma function;
V represents a variance; and
$(Y_{0.10}|S)$ represents a confidence limit at stress S for the $100q^{th}$ percentile with q=0.10.

34. The method of claim 33, wherein the step of computing the Load Enhancement Factor further comprises solving for $S_E$ through the equation:

$$S_E = \exp\left(\frac{\ln(X_I) - \ln(\Gamma(1 + 1/\hat{\beta}_{SN})) - \hat{\theta}_0}{\hat{\theta}_1}\right)$$

wherein:
$X_I$ being the number of cycles that defines one lifetimes
$\theta_0$ represents the intercept parameter of the Weibull regression model; and
$\theta_1$ represents the slope parameter of the Weibull regression model.

35. The method of claim 34, wherein the step of computing the Load Enhancement Factor further comprises solving for $S_B$ through the equation:

$$X_I = \exp[\hat{\theta}_0 + \hat{\theta}_1 \ln(S_B)]\exp\left[C_{0.10}\hat{\sigma} - 1.645\sqrt{V(\hat{Y}_{0.10}|S_B)}\right]$$

and using a nonlinear solver on the equation
wherein:
$\theta_0$ represents an intercept parameter of the Weibull regression model;
$\theta_1$ represents a slope parameter of the Weibull regression model;
$S_B$ represents a stress level computed from a B-basis value of fatigue cycle distribution;
$\sigma = 1/\beta_{SN}$;
$(Y_{0.10}|S)$ represents a confidence limit at stress S for the $100q^{th}$ percentile with q=0.10; and
$C_q = \ln(-\ln(1-q))$.

36. The method of claim 35, wherein the computation of the Load Enhancement Factor includes calculating a Life factor described in equation:

$$N_F = \frac{\Gamma(1 + 1/\hat{\beta}_{SN})}{\exp\left[C_{0.10}\hat{\sigma} - 1.645\sqrt{V(\hat{Y}_{0.10}|S_B)}\right]}$$

and calculating $S_A$ by solving equation:

$$X_I = \exp\left[\hat{\theta}_0 + \hat{\theta}_1 \ln(S_A) + C_{0.01}\hat{\sigma} - 1.645\sqrt{V(\hat{Y}_{0.01}|S_A)}\right]$$

and imposing $LEF(N_F)=1$, the computation computing the ratio under the following equations:

$$K(N_F) = \frac{S_B}{S_E} = \frac{S_B}{\exp[\{\ln(X_I) - \ln(\Gamma(1 + 1/\hat{\beta}_{SN})) - \hat{\theta}_0\}/\hat{\theta}_1]}$$

and $K(N_F) = (N_F)^{1/\hat{\theta}_1}$
and the computation of LEF based on Weibull regression being expressed by the equation:

$$LEF(N_0) = \frac{S_E}{S_B}(N_0)^{1/\hat{\theta}_1} = \frac{\exp(-\hat{\theta}_0/\hat{\theta}_1)}{S_B}\left(\frac{X_I N_0}{\Gamma(1 + 1/\hat{\beta}_{SN})}\right)^{1/\hat{\theta}_1},$$

wherein LEF is computed using the equation for LEE ($N_0$) and the equation for $S_B$
wherein:
$S_A$ represents a stress level computed from an A-basis value of a fatigue cycle distribution;

$K(N_F)$ represents a scaling function for Life Factor $N_F$; and $K(N_0)$ represents a scaling for given lifetime $N_0$.

37. A method of evaluating a composite component of an aircraft, comprising the steps of:

calculating a Load Enhancement Factor of the composite component of the aircraft using Modified Joint Weibull Analysis, wherein calculating the Load Enhancement Factor comprises the steps of:

retrieving a test data set from at least one database;

analyzing the retrieved test data of the test data set for fit with a Weibull regression model;

computing at least one scale parameter for the Weibull regression model;

calculating a stress to life cycle relationship accounting for scatter in the retrieved test data through the Weibull regression model of the retrieved test data by relating a log of the scale parameter of the Weibull regression model with a log of a stress level of a stress to life cycle relationship; and calculating, using a processor, the Load Enhancement Factor as a function of a slope and an intercept of the stress to life cycle relationship.

* * * * *